US010064967B2

(12) United States Patent
Nguyen

(10) Patent No.: US 10,064,967 B2
(45) Date of Patent: Sep. 4, 2018

(54) ADJUSTABLE ULTRAVIOLET LED STERILIZATION AUTOMATIC ENCLOSURE

(71) Applicant: Nathan Nguyen, Garden Grove, CA (US)

(72) Inventor: Nathan Nguyen, Garden Grove, CA (US)

(*) Notice: Subject to any disclaimer, the term of this patent is extended or adjusted under 35 U.S.C. 154(b) by 0 days.

(21) Appl. No.: 15/903,885

(22) Filed: Feb. 23, 2018

(65) Prior Publication Data

US 2018/0221520 A1 Aug. 9, 2018

Related U.S. Application Data

(63) Continuation of application No. 15/890,205, filed on Feb. 6, 2018.

(60) Provisional application No. 62/455,956, filed on Feb. 7, 2017.

(51) Int. Cl.
*A61L 2/24* (2006.01)
*A61L 2/10* (2006.01)

(52) U.S. Cl.
CPC .............. *A61L 2/10* (2013.01); *A61L 2/24* (2013.01); *A61L 2202/14* (2013.01)

(58) Field of Classification Search
CPC ........... A61L 2/10; A61L 2/24; A61L 2202/14
See application file for complete search history.

(56) References Cited

U.S. PATENT DOCUMENTS

| 6,297,047 | B1* | 10/2001 | Butts | A61L 2/10 |
| | | | | 219/400 |
| 6,605,260 | B1* | 8/2003 | Busted | A61L 2/10 |
| | | | | 422/186.07 |
| 8,084,752 | B2 | 12/2011 | Ranta et al. | |
| 2004/0170525 | A1* | 9/2004 | Ettlinger | B08B 15/02 |
| | | | | 422/24 |
| 2008/0067417 | A1* | 3/2008 | Lane | A61L 2/10 |
| | | | | 250/455.11 |
| 2009/0218512 | A1* | 9/2009 | Ranta | A61L 2/10 |
| | | | | 250/455.11 |

* cited by examiner

*Primary Examiner* — Sean E Conley
(74) *Attorney, Agent, or Firm* — Snell & Wilmer LLP

(57) ABSTRACT

A sterilization enclosure includes a main body defining a volume and having a movable component configured to move between an access position to allow access to the volume and a restricted position to at least partially enclose the volume. The sterilization enclosure further includes a light source located in the volume and configured to emit light having a frequency that injures pathogens. The sterilization enclosure further includes a switch coupled to the movable component and configured to be in a closed position to allow power to flow to the light source to cause the light source to emit the light into the volume when the movable component is in the closed position.

18 Claims, 23 Drawing Sheets

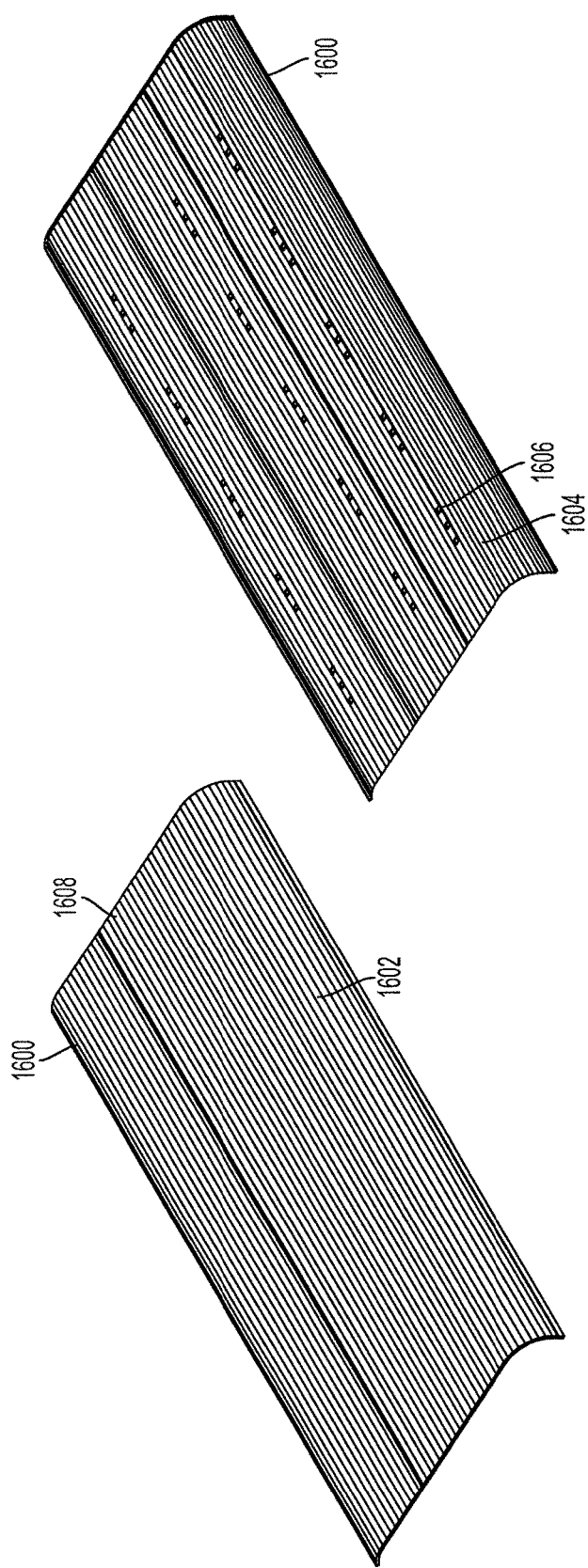
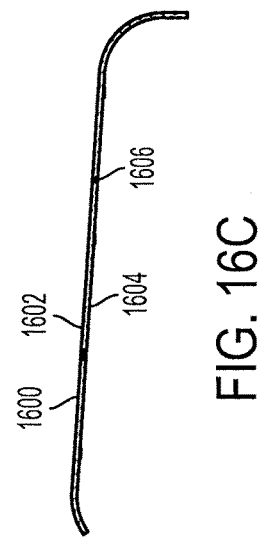
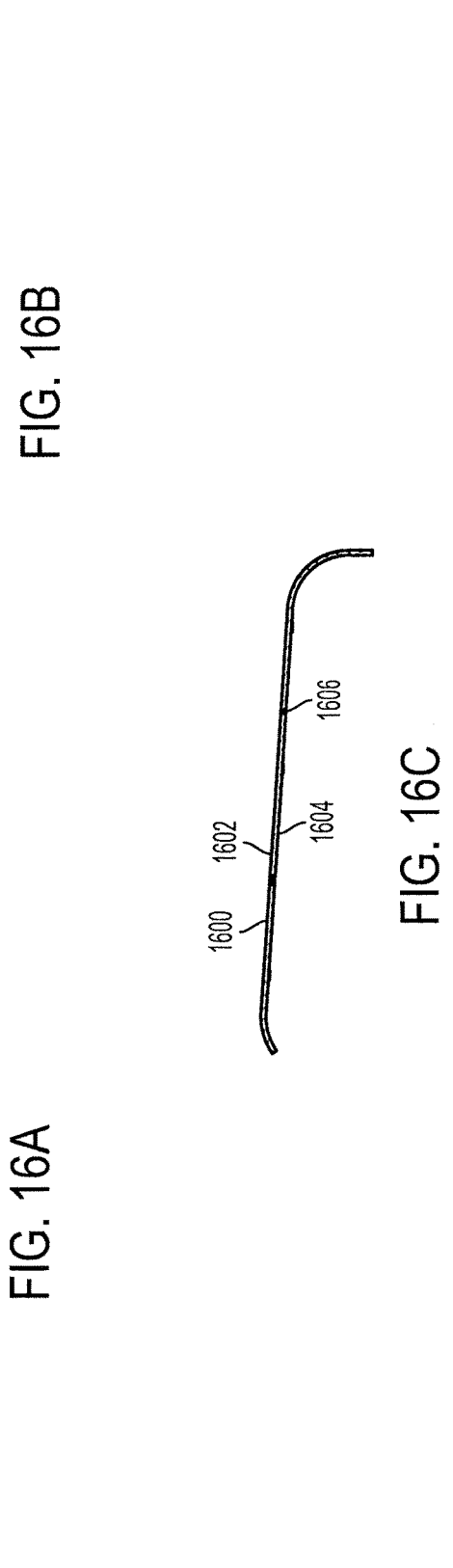
FIG. 16A
FIG. 16B
FIG. 16C

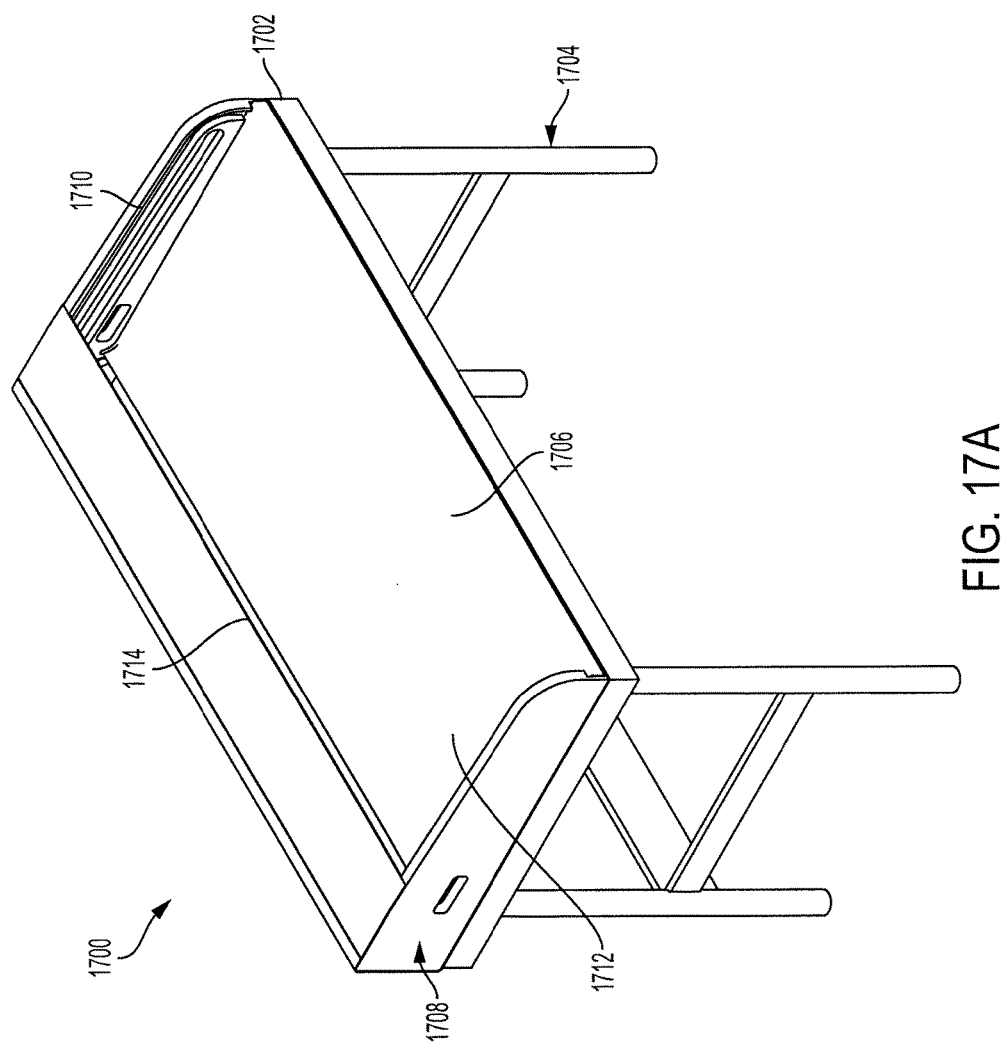

the benefit and priority of U.S. Provisional Application No. 62/455,956, titled ADJUSTABLE ULTRAVIOLET LED STERILIZATION AUTOMATIC ENCLOSURE, filed on Feb. 7, 2017, the entire contents of both being hereby incorporated by reference in their entirety.

ADJUSTABLE ULTRAVIOLET LED STERILIZATION AUTOMATIC ENCLOSURE

CROSS REFERENCE TO RELATED APPLICATIONS

This application claims the benefit and priority of U.S. patent application Ser. No. 15/890,205, titled ADJUSTABLE ULTRAVIOLET LED STERILIZATION AUTOMATIC ENCLOSURE, filed on Feb. 6, 2018, which claims the benefit and priority of U.S. Provisional Application No. 62/455,956, titled ADJUSTABLE ULTRAVIOLET LED STERILIZATION AUTOMATIC ENCLOSURE, filed on Feb. 7, 2017, the entire contents of both being hereby incorporated by reference in their entirety.

BACKGROUND

Field

The present disclosure is directed to systems and methods for sterilizing materials used by multiple individuals.

Description of the Related Art

With population density and global travel increasing rapidly, health epidemics are becoming a serious concern. One such tool against spread of disease is sterilization of surfaces. However, conventional surface sterilizing devices may be ineffective, may have insufficient sterilization power, and may be too big or clumsy to sterilize germs, viruses and bacteria on object surfaces like door handles, sponges, cutting boards, dish racks, elevator buttons, keyboards, mouse pads.

Thus, there is a need in the art for a sterilization device capable of use in multiple situations to destroy pathogens such as germs, viruses, and bacteria.

SUMMARY

Disclosed herein is a sterilization enclosure. The sterilization enclosure includes a main body defining a volume and having a movable component configured to move between an access position to allow access to the volume and a restricted position to at least partially enclose the volume. The sterilization enclosure further includes a light source located in the volume and configured to emit light having a frequency that injures pathogens. The sterilization enclosure further includes a switch coupled to the movable component and configured to be in a closed position to allow power to flow to the light source to cause the light source to emit the light into the volume when the movable component is in the closed position.

Also disclosed is another sterilization enclosure. The sterilization enclosure includes a main body defining a volume and having a retractable cover having a retracted position that allows access to the volume and an extended position that restricts access to the volume. The sterilization enclosure further includes a light source located in the volume and configured to emit light having a frequency that injures pathogens. The sterilization enclosure further includes a controller coupled to the light source and configured to cause the light source to emit the light when the retractable cover is in the extended position.

Also disclosed is a sterilization enclosure. The sterilization enclosure includes a retractable cover having an inner surface. The sterilization enclosure further includes a plurality of light emitting devices positioned on the inner surface and configured to output ultraviolet light having a wavelength that is capable of sterilization. The sterilization enclosure further includes a motion sensor configured to detect motion. The sterilization enclosure further includes a controller coupled to the retractable cover, the plurality of light emitting devices, and the motion sensor and configured to control the retractable cover to retract and to control the plurality of light emitting devices to output the ultraviolet light based on data detected by the motion sensor.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIGS. 16A, 16B, and 16C are drawings illustrating a top side, a bottom side, and a side view respectively, of a retractable cover for use with a sterilization enclosure according to various embodiments of the present disclosure;

FIGS. 17A and 17B are drawings illustrating a sterilization enclosure capable of being used as a desk according to various embodiments of the present disclosure;

DETAILED DESCRIPTION

Figure 1:
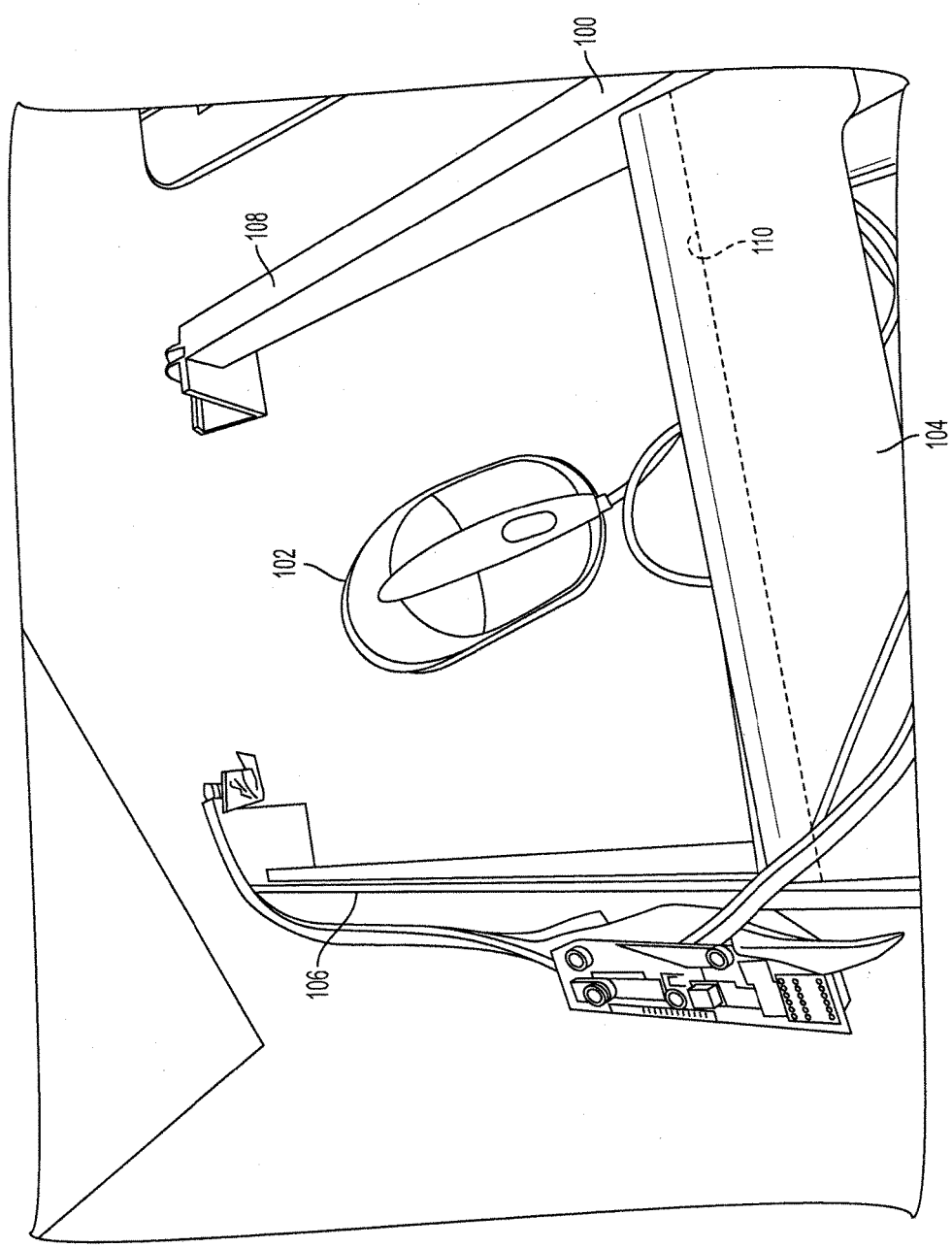
FIG. 1 is a drawing of a sterilization enclosure with a movable component in an access position according to various embodiments of the present disclosure.

Other systems, methods, features, and advantages of the present invention will be or will become apparent to one of ordinary skill in the art upon examination of the following figures and detailed description.

The present invention seeks to provide a solution to this problem by providing an effective pathogen (i.e., germ, bacteria, virus, mold, parasite, and the like) sterilizer. The sterilizer may be customizable and space saving, and may have water resistant properties. The sterilizer may use LED (or other UV-C) germicidal UV short wavelength (i.e., between 230 and 310 nm, between 240 and 300 nm, between 255 and 280 nm, or the like) ultraviolet light sources. The sterilizer may be adjustable (by a user) to fit desired objects such as door handles, sponges, cutting boards, dish racks, elevator buttons, keyboards, computer mice, and mouse pads.

The adjustable, customizable ultraviolet germicidal sterilizer device may include an automatic door or other opening that is activated by motion. For example, the device may include a motion sensor that detects when a user is within a predetermined area of the device, a motion sensor that detects when the user waves their hands over the motion sensor (i.e., detects a certain gesture), or an activation button. In some embodiments, the device may activate the closing mechanism for a period of time, such as between 5 and 30 seconds, or 5 and 15 seconds, or about 10 seconds (10 seconds plus or minus 10 percent) seconds, and turn on all the ultraviolet LED (UVC) germicidal UV short wavelength ultraviolet sterilization light sources or tube lights to sterilize germs, viruses, bacteria, molds and other microorganisms. After a predetermined period of time (such as 10 seconds), the device may automatically open to provide access to the sterilized device that is now free of harmful viruses, bacteria, germs, molds and other microorganisms.

In some embodiments, the device may be provided in three different sizes: large, medium and small. The large size may have an adjustable length between 12 inches and 20 inches. The medium size may have an adjustable length between 8 inches and 14 inches. The small size may have an adjustable length between 5 inches and 8 inches. The device can be adjustable to a rectangular or square shape depending on the object needs. In some embodiments, the device may be adjustable to other shapes, such as triangular, circular, octagonal, or the like. Likewise, the height may be adjustable, such as from 2 inches to 6 inches.

In some embodiments, the ultraviolet wet/dry surface sterilizer device is adjustable, customizable to fit the user-desired objects with three different sizes, large, medium and small with an automatic motion activated lid enclosure. The user may activate the ultraviolet LED (UVC) germicidal UV short wavelength 255-280 nm ultraviolet sterilization light source or tube light to sterilize germs, viruses, bacteria, molds and other microorganisms. After a period of time, such as 10 seconds, the device may automatically open to let the user use the sterilize device free of harmful viruses, bacteria, germs, molds and other microorganisms. The ultraviolet sterilization device may be activated a hand gesture to activate the automatic lid that may slide or otherwise move to close the device and activate the ultraviolet LED (UVC) germicidal UV short wavelength ultraviolet sterilization light source or tube light for a period of time. This may effectively sterilize mutagenic to harmful germs, bacteria, virus, molds, and other microorganisms or pathogens inside the device and sterilize the object such that it is safe to touch by a user without transmitting any of the above germs, bacteria, or the like.

Referring to FIG. 1, an image of an exemplary sterilization device 100 is shown. In FIG. 1, the device 100 is being used to sterilize a mouse 102. The device 100 includes a cover 104, a back portion 110, and two side portions 106, 108. In some embodiments, the cover 104, the back portion 110, and the two side portions 106, 108 may each include one or more of a metal, a plastic, a rubber, or any other natural or synthetic material.

The cover 104 of the device 100 provides advantages. For example, the cover protects organs of humans (eyes, skin, etc.) along with sensitive objects from the ultraviolet light output by the device 100. For example, the light output by the device 100 may be harmful to human organs.

In some embodiments, the device 100 may have an adjustable size. In that regard, a length, width, and/or height of the device 100 may be adjustable within a predetermined range. In some embodiments, the adjustment may be made by hand and, in some embodiments, the adjustment may be made electronically such as by a motor.

Figure 2:
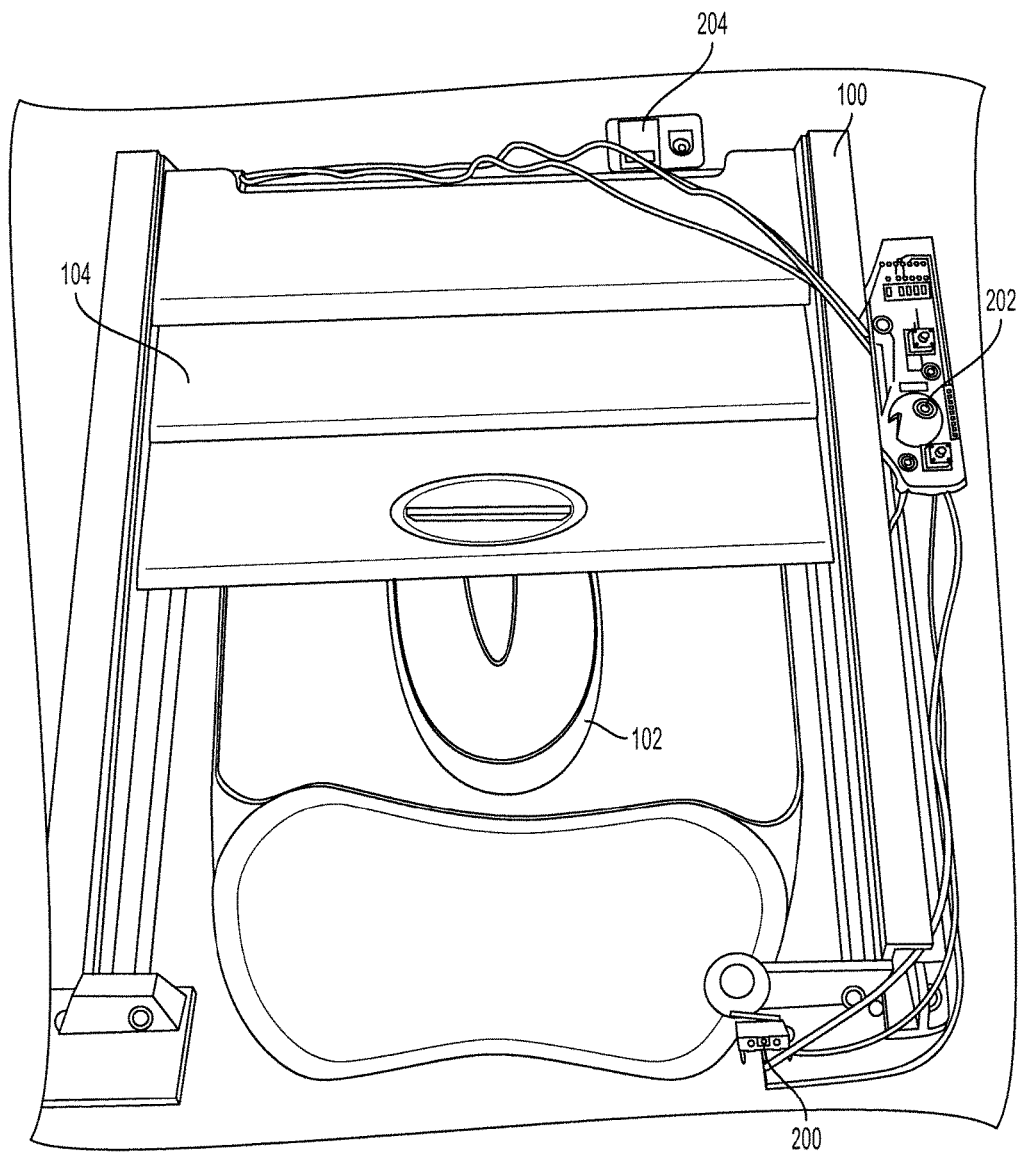
FIG. 2 is a drawing of the sterilization enclosure of FIG. 1 with the movable component in a partially restricted position according to various embodiments of the present disclosure.

Turning to FIG. 2, the device 100 may include multiple sensors. In particular, the device 100 may include a presence detector 200 and a motion sensor 202. The device 100 may be activated based on data detected by one or both of the presence detector 200 or the motion sensor 202. In some embodiments, the cover 104 of the device 100 may remain closed until the presence of a person is detected by the presence detector 200. When the presence is detected, the cover 104 may be actuated by a motor 204 such that it opens to provide access to the mouse 102. In that regard, the motion sensor 202 may include any type of motion or other sensor such as an ultrasonic sensor, a proximity sensor, an infrared sensor, a vibration sensor, a microwave sensor, a dual technology motion sensor, an area reflective type sensor, or the like.

The motor 204 may include any type of motor capable of actuating the cover 104, such as a brushless motor, a permanent magnet motor, a wound motor, an asynchronous motor, a one phase motor, or a multiple phase motor. In that regard, the motor 204 may operate based on direct current (DC) or analog current (AC) power. When the presence of the person is no longer detected, the motor 204 may close the cover 104 and one or more ultraviolet LED UV short wavelength light emitter may generate light for a predetermined period of time to sterilize the mouse 102.

In some embodiments, the cover 104 may remain open until motion, such as a hand wave or other gesture, is detected by the motion sensor 202. In some embodiments, the cover 104 may close and the LED light emitters may emit light to sterilize the mouse 102 in response to the motion being detected. After a predetermined period of time, the cover 104 may reopen to allow access to the sterilized mouse 102.

Figure 3:
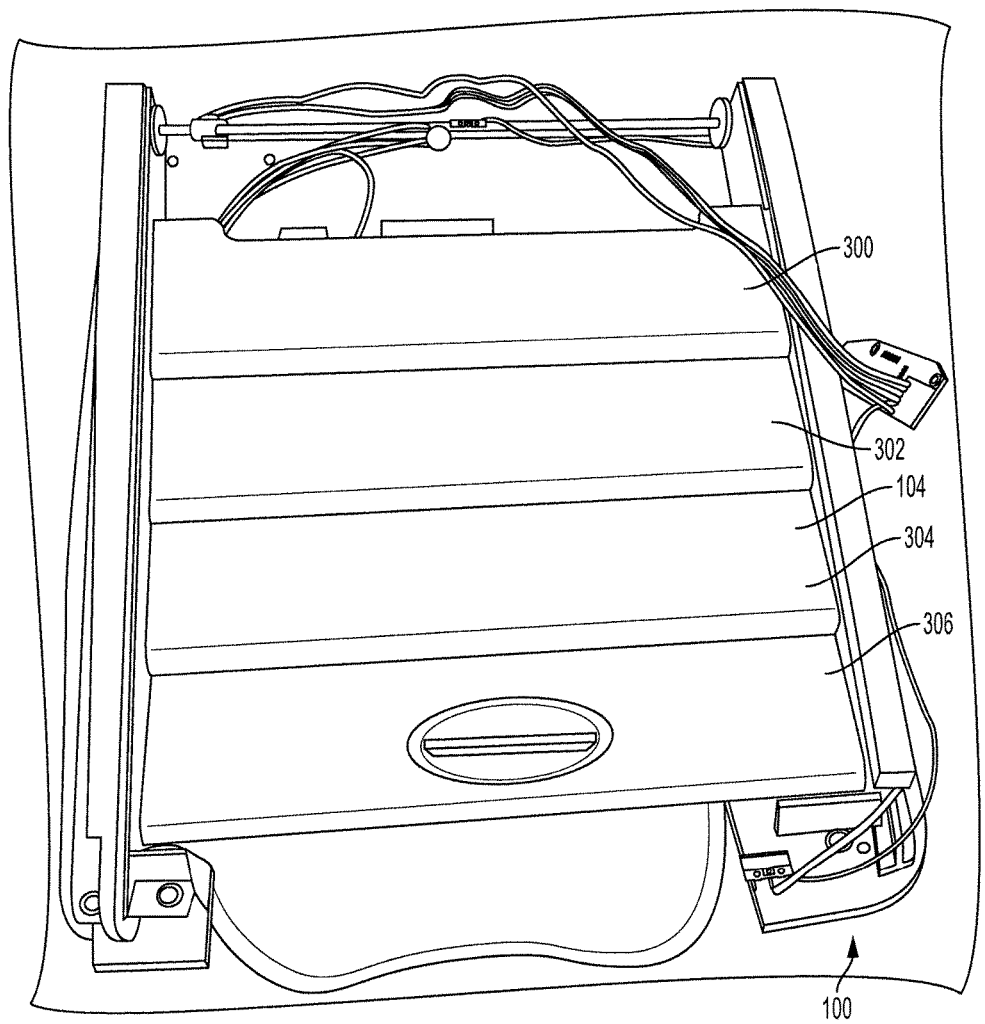
FIG. 3 is a drawing of the sterilization enclosure of FIG. 1 with the movable component n a restricted position according to various embodiments of the present disclosure.

Referring now to FIG. 3, device 100 may be in a closed state. In that regard, the retractable cover 104 is covering the mouse. The cover 104 may include multiple panels including a $1^{st}$ panel 300, a $2^{nd}$ panel 302, a $3^{rd}$ panel 304, and a $4^{th}$ panel 306. When the cover 104 is closed, as shown in FIG. 3, each of the panels 300, 302, 304, 306 may be positioned adjacent to each other along a length of the device 100. When the cover 104 is open, as shown in FIG. 1, each of the panels 300, 302, 304, 306 may be stacked above each other along a height of the device 100.

Figure 4:
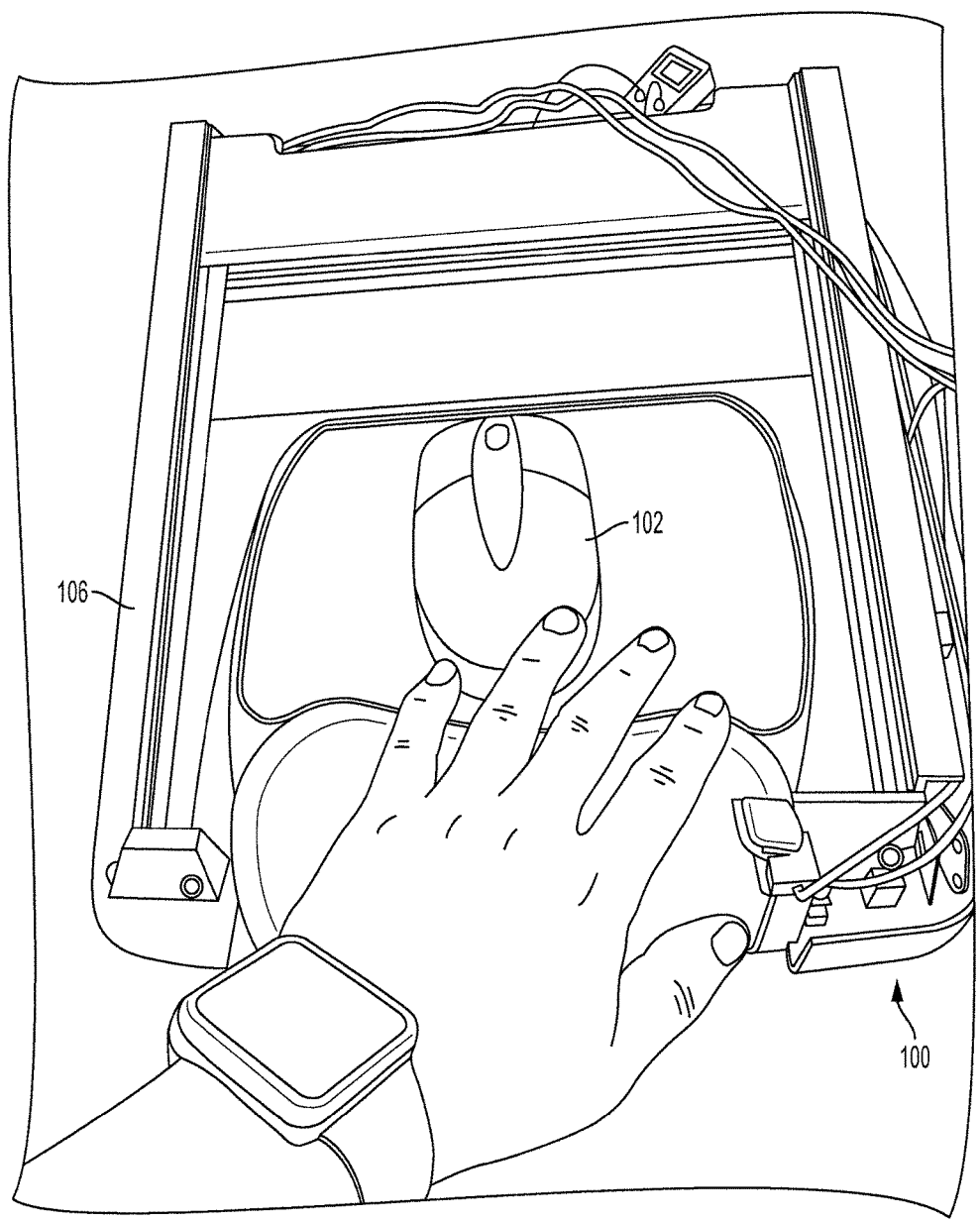
FIG. 4 is a drawing of the sterilization enclosure of FIG. 1 illustrating access to sterilized components within the sterilization enclosure according to various embodiments of the present disclosure.

Turning to FIG. 4, the mouse 102 may be accessible when the cover 104 is open. Accordingly, a user may use the mouse 102 without fear of being exposed to pathogens after sterilization by the device 100. When the user moves from the location in front of the device 100, one or more sensor may detect that the person has left. At that point, a controller may cause the cover 104 to close and the light source to emit the light, thus sterilizing the mouse 102 for use by another person. In that regard, use of the device 100 provides for automatic sterilization of any item positioned within the sides 106, 108 and the cover 104.

Figure 5:
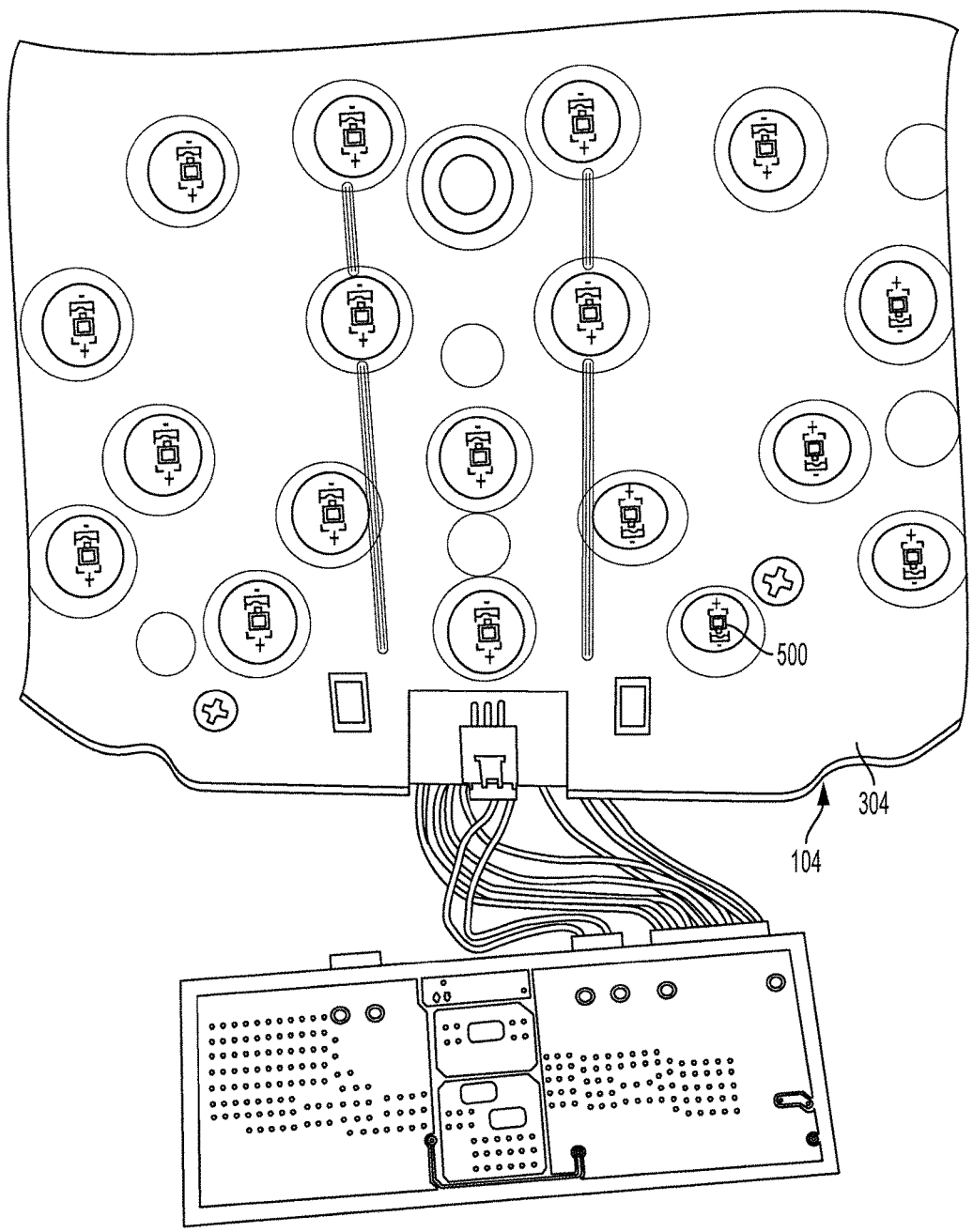
FIG. 5 is a drawing illustrating an inside surface of a retractable cover of the sterilization enclosure of FIG. 1 that includes multiple light sources capable of emitting light at a frequency that injures pathogens according to various embodiments of the present disclosure.

Turning now to FIG. 5, a view of an inside of the panel 304 of the cover 104 is shown. The inside of the panel 304 is the surface of the panel 304 that is oriented towards the mouse 102 when the cover 104 is closed. As shown, the panel 304 includes a plurality of LED devices 500. Each of the LED devices 500 may include a germicidal ultraviolet short wavelength LED emitter capable of emitting light having a wavelength of between 240 and 310 nm, between 250 and 300 nm, between 255 and 280 nm, or the like. Light within this range of wavelengths may be capable of sterilizing a surface which is exposed to the light. In that regard, exposure to the light emitted by each of the LED devices 500 may damage or destroy viruses, bacteria, germs, molds, and other microorganisms.

In some embodiments, one or more of the cover 104, the sides 106, 108, the back portion 110, and the LED devices 500 may be waterproofed. For example, one or more of these components may be covered in a waterproof resin.

In some embodiments, one or more of the cover 104, the sides 106, 108, the back portion 110, and the LED devices 500 may include a reflective coating. This may allow the light emitted by the LED devices 500 to more effectively contact all surfaces of items within the device 100.

In some embodiments and referring to FIGS. 1 and 5, an interior surface of the sides 106, 108 may also include LED devices 500. Furthermore, the device 100 may include a back side 110 that also has an inner surface having LED devices 500.

Figure 6:
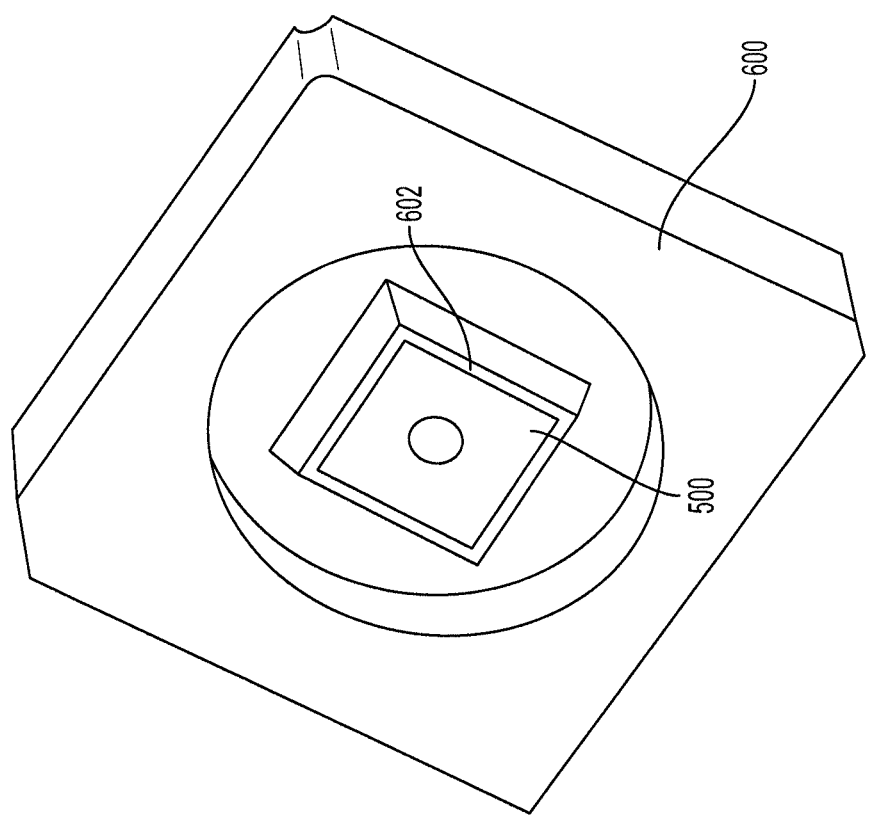
FIG. 6 is a drawing illustrating a light source capable of emitting light at a frequency that injures pathogens according to various embodiments of the present disclosure.

Turning to FIG. 6, an enlarged view of one of the LED devices 500 is shown. As shown, the LED device 500 has a body 600 and a light-emitting portion 602. In some embodiments, the body 600 may be mounted to an inner surface of a portion of the device 100 and the light-emitting portion 602 may be oriented inward from the surface. The light-emitting portion 602 may emit the ultraviolet light having the desirable wavelength.

Figure 7:
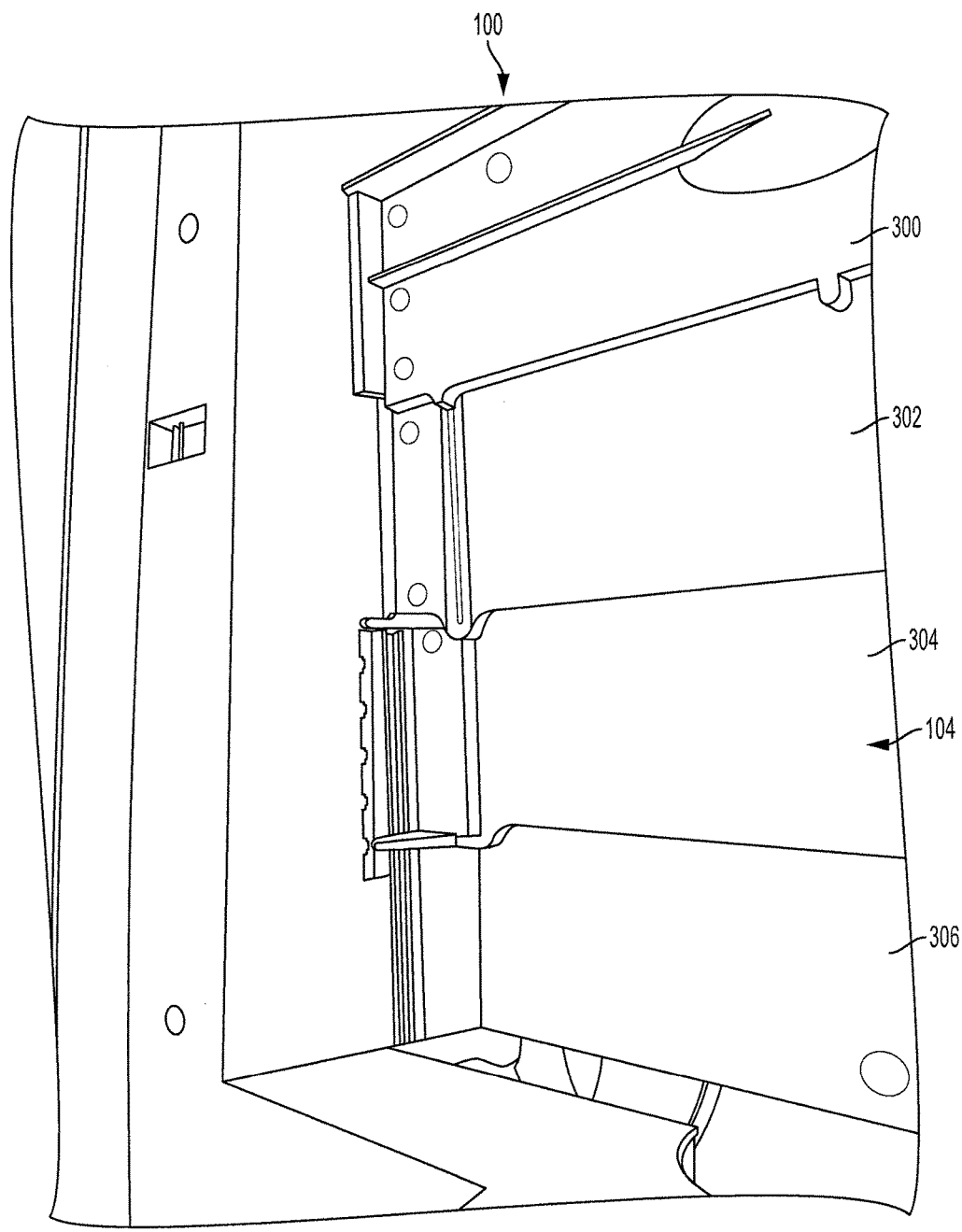
FIG. 7 is a drawing illustrating an underside of the sterilization enclosure of FIG. 1 with the movable component in the restricted position according to various embodiments of the present disclosure.

Turning now to FIG. 7, a view of an inner surface of the cover 104 is shown. As shown, each panel 300, 302, 304, 306 of the cover 104 may be positioned such that the panels 300, 302, 304, 306 may be positioned adjacent to each other along a length of the device 100 when the cover 104 is closed, and may be stacked above each other when the cover 104 is open.

Figure 8:
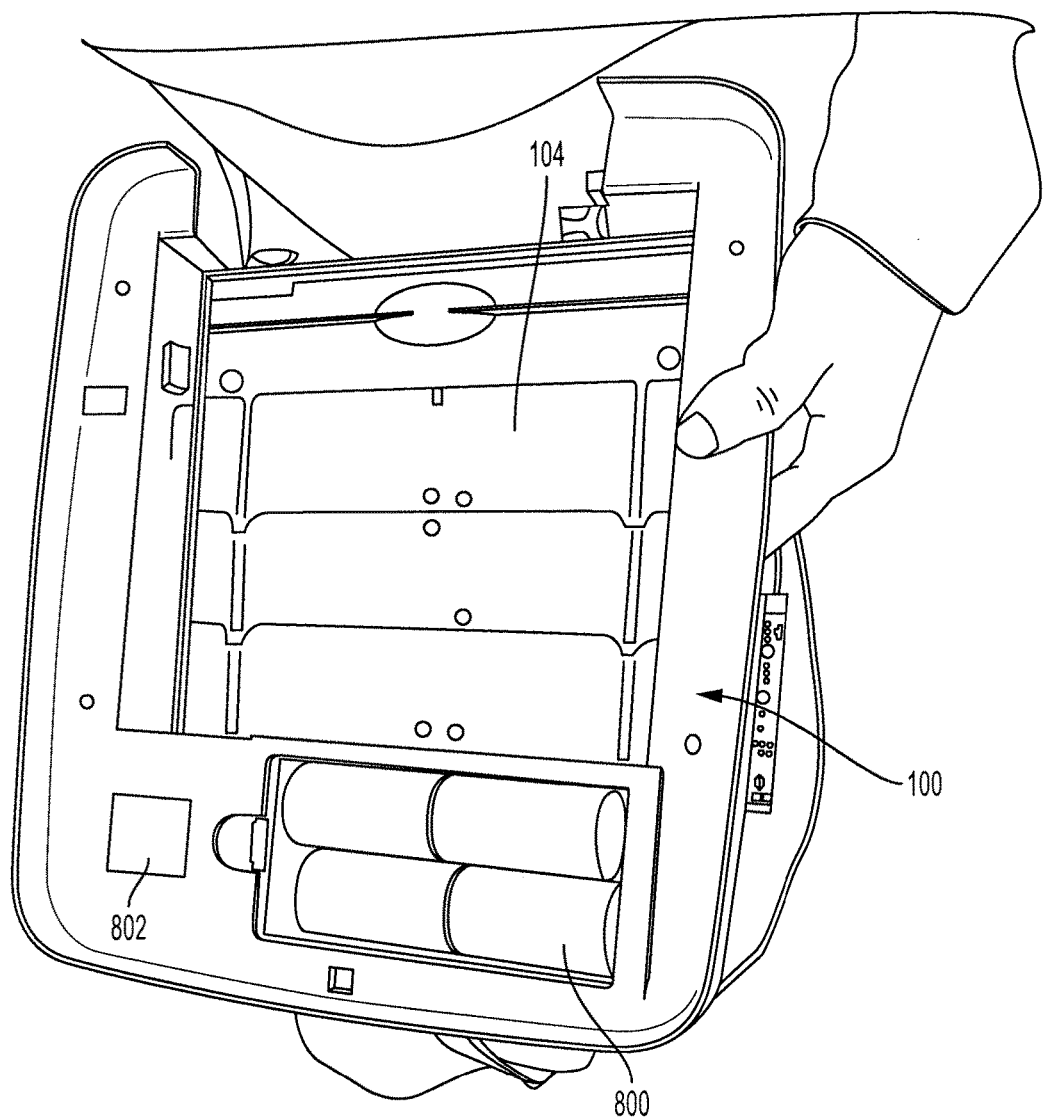
FIG. 8 is a drawing illustrating a sterilization enclosure capable of operating using battery power according to various embodiments of the present disclosure.

Turning to FIG. 8, the device 100 may be powered via batteries 800 or a power source 802. The power source 802 may be designed to be coupled to an external power source, such as a wall outlet. In some embodiments, the device 100 may be powered via one or both of the batteries 800 and the power source 802. In some embodiments, the batteries 800 may be recharged when the device 100 is coupled to the power source 802.

Figure 9:
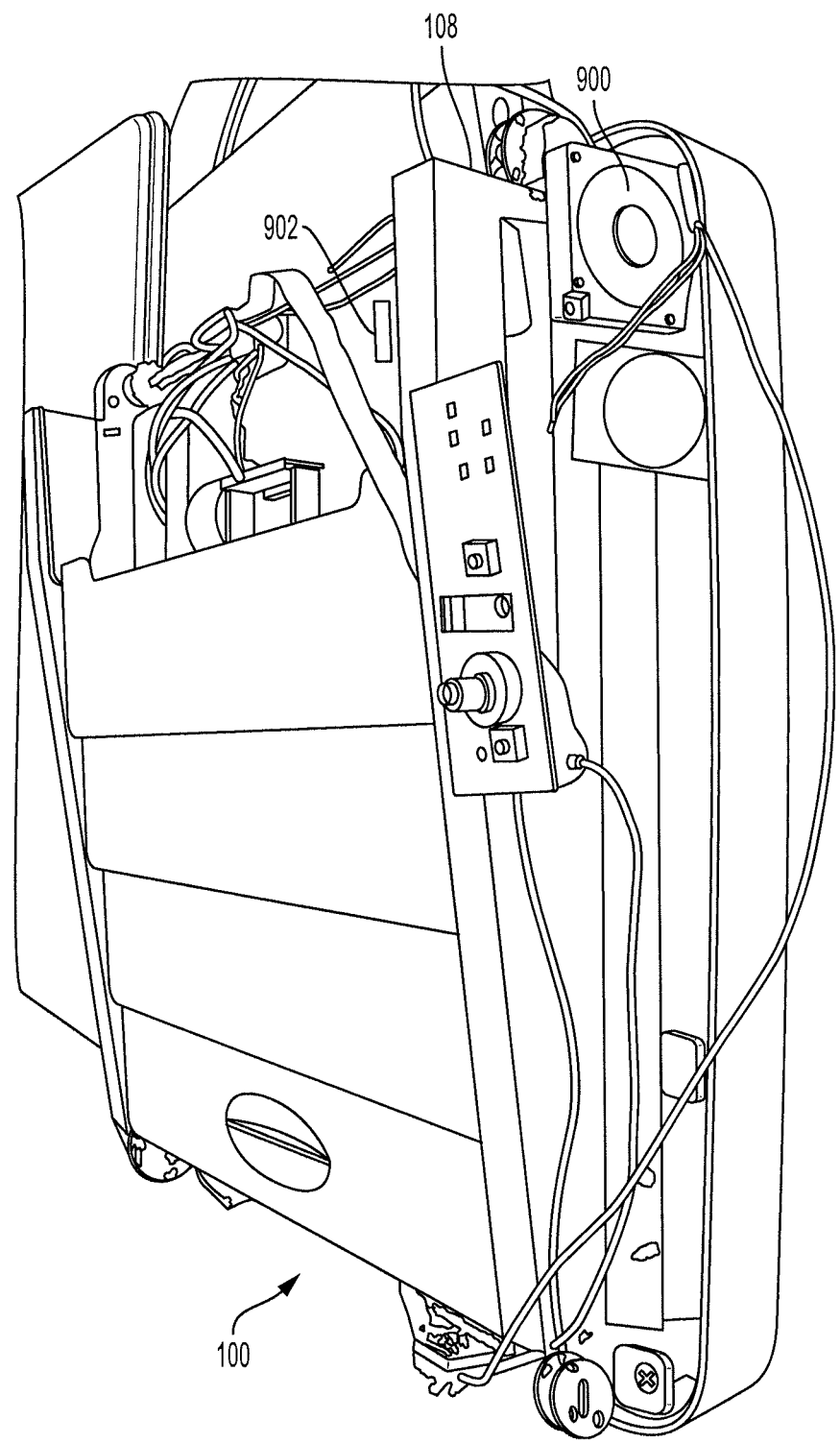
FIG. 9 is a side view of the sterilization enclosure of FIG. 8 according to various embodiments of the present disclosure.

Turning to FIG. 9, the device 100 may be capable of sterilizing ambient air as well as any object located within the device 100. In that regard, the device 100 may include a fan 900 positioned on a side 108. The fan 900 may draw air into a chamber defined within the device 100. The device 100 may include a tube LED 902 also capable of outputting light having a wavelength of between 240 and 310 nm, between 250 and 300 nm, between 255 and 280 nm, or the like. The device 100 may further define an outlet.

As the air is drawn into the chamber via the fan 900, the air is exposed to the ultraviolet light from the tube LED 902. As the air is exposed to this ultraviolet light, it is sterilized. As more air is drawn into the chamber via the fan 900, the sterilized air may be displaced out of the device 100 via the outlet. Accordingly, ambient air may continue being drawn into the device 100 and sterilized. In some embodiments, the fan 900 may force air out of the device 100. In that regard, the fan 900 may be said to draw air into the chamber via the "outlet."

Figure 10:
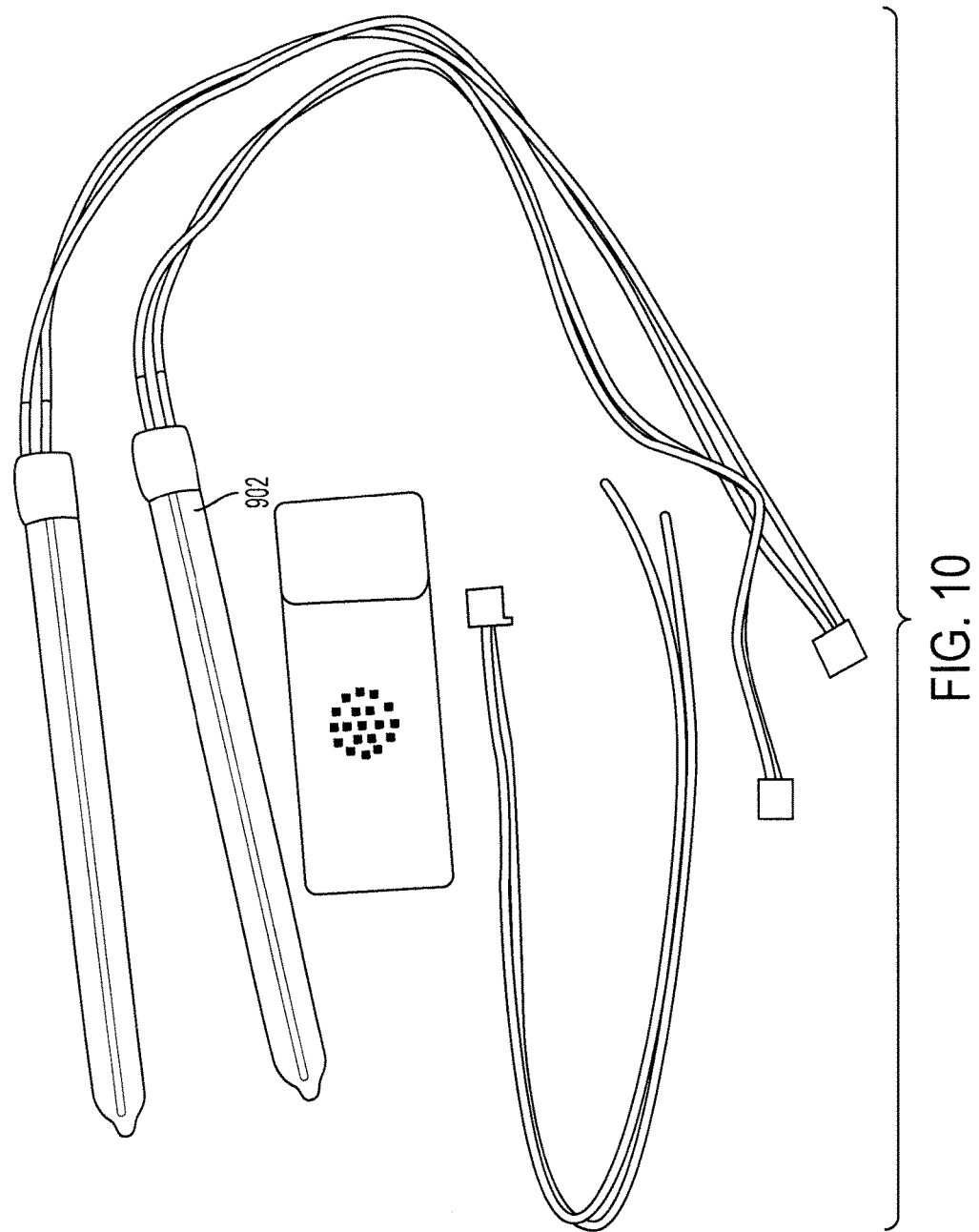
FIG. 10 is a drawing illustrating a light source capable of emitting light having a frequency that injures pathogens according to various embodiments of the present disclosure.

Turning now to FIG. 10, the tube LED 902 may have a tubular shape. The tubular shape of the tube LED 902 may create a relatively large amount of surface area. The relatively large surface area allows the light emitted by the tube LED 902 to sterilize a relatively large volume of air at any given time.

Figure 11:
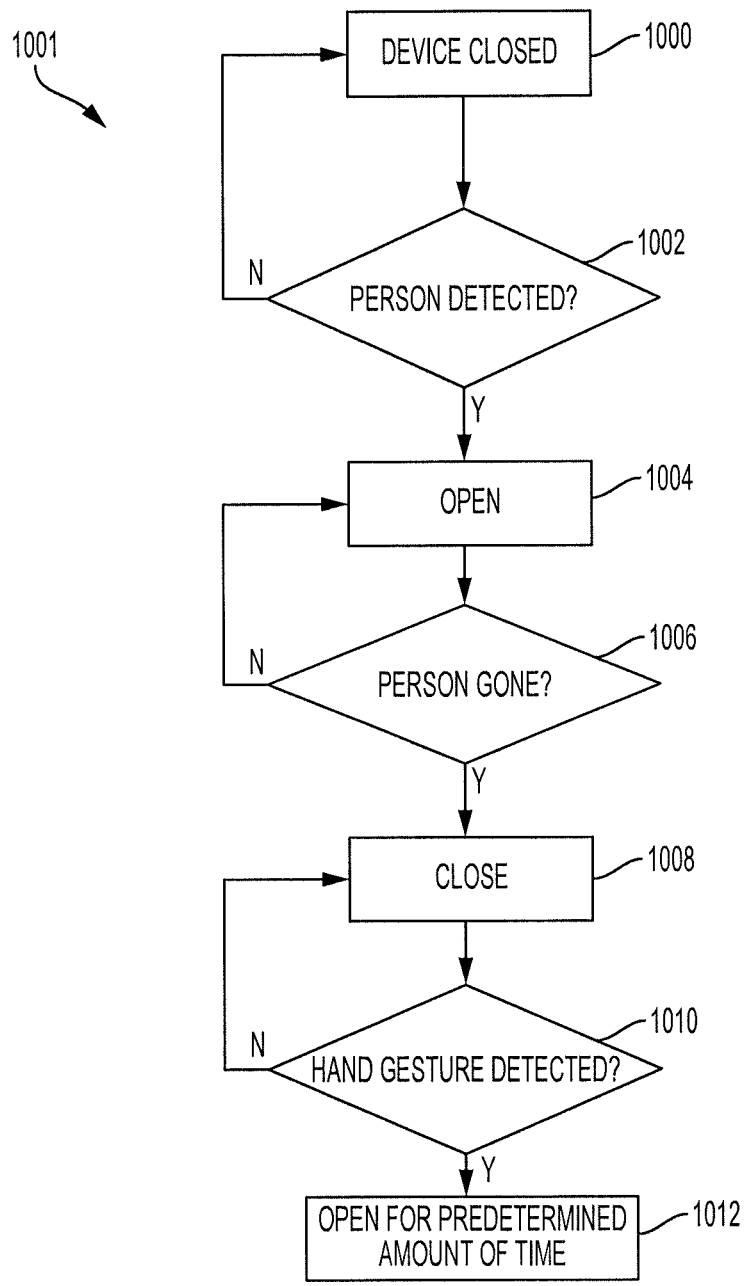
FIG. 11 is a flowchart illustrating a method for sterilizing items with which multiple persons come into contact according to various embodiments of the present disclosure.

Turning now to FIG. 11, a flowchart illustrating a method 1001 for control of the device 100 or another sterilization enclosure is shown. In some embodiments, the device 100 may include a processor or controller capable of implementing the method 1001.

In block 1000, a sterilization enclosure, such as the device 100, may begin in a closed position. In block 1002, it may be determined whether a person is detected by a presence sensor of the device. If no person is detected then the method 1001 may return to block 1000. However, if a person is detected, the method 1001 may proceed to block 1004 where the device becomes open. When the device becomes open, the user may access any object previously sterilized by the device. In some embodiments, the device may remain in the open position until a certain event, such as a gesture.

In block 1006, the presence sensor may detect whether the person is no longer in the vicinity of the device. If the person is still within the vicinity of the device, the device may remain open in block 1004. However, if the person is no longer detected, the method 1001 may proceed to block 1008. In block 1008, the device may close. Furthermore, when the device closes, the device may emit sterilizing light to sterilize any object located within the device.

In block 1010, a motion detector may detect whether a particular hand gesture has occurred. The hand gesture may correspond to a request by the user for the device to open to allow access to the object. If the hand gestures detected in block 1010, the method 1001 may proceed to block 1012 where the device may open, such as for a predetermined amount of time or until another hand gesture is detected.

Additional or alternative operation of the device may also occur. For example, the device may be open during steady state. The device may close and emit sterilizing light for a period of time after detecting a hand gesture. In that regard, a person may place an object within the device and may make the hand gesture to cause the device to close for a period of time and sterilized the object. After expiration of the period of time, the device may reopen to allow access to the object.

In some embodiments, the device may operate differently when a person is detected versus when a hand gestures detected. For example, the device may close in response to a hand gesture in order to sterilize an object. The same device may begin to sterilize air when the presence of a person is detected.

In some embodiments, the device may be capable of wirelessly communicating with a remote device. For example, the device may be controllable via Wi-Fi, Bluetooth, or another wireless protocol. In that regard, a user may control the device via a remote device. For example, when the device is used in a classroom, it may be designed to cover a keyboard and/or mouse used by students. In order to prevent distraction to the students, the mouse and/or keyboard may be covered by the device until their use is desired. When use of the keyboard or mouse is desired, the teacher or professor may wirelessly control the device to open to allow access to the keyboard or mouse. In some embodiments, the wireless access may also be used to for additional activities. For example, the device may determine when maintenance is required and send an alert to an appropriate person. Likewise, the device may measure usage data (such as when the device is open or closed) and may report such usage data to an administrator.

In some embodiments, the device may include a filter. The filter may capture pollen, dust, or other debris that is contained within air that is drawn through the device. In that regard, the filter may further improve ambient air quality.

In some embodiments, each of the LED devices 500 and/or the tube LED 902 may be removed and/or replaced relatively easily. Accordingly, if one or more LED burns out, a replacement may be inserted with relative ease.

In some embodiments, one or more of the interior surfaces (where the LED devices 500 are located) may have a reflective surface. The reflective surface may increase the distribution of the sterilizing ultraviolet light within the device.

In some embodiments, the device may be designed for a specific use. For example, the device may be designed to be positioned around a door handle. In that regard, the device may define one or more openings for receiving the door handle and/or mounting the device to a location on the door near the door handle.

Figure 12:
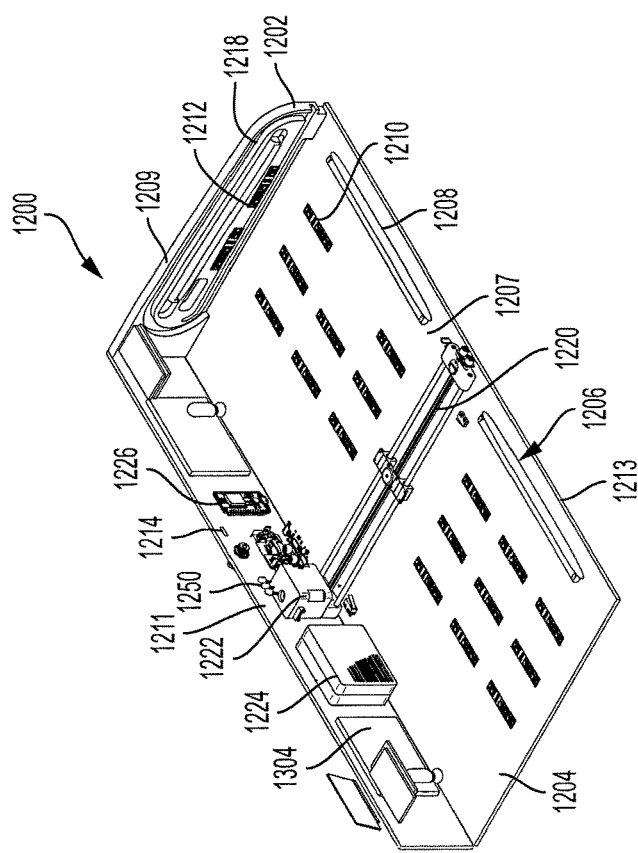
FIG. 12 is a drawing of a sterilization enclosure having multiple light sources capable of emitting light at a frequency that injures pathogens according to various embodiments of the present disclosure.

Turning to FIG. 12, another sterilization enclosure 1200, also referred to as a device 1200, is shown. The sterilization enclosure 1200 includes a main body 1202 that defines a cavity 1204. The sterilization enclosure 1200 may be designed to sterilize (i.e., damage or otherwise injure) pathogens such as microbes, viruses, bacteria, or the like. In that regard, the sterilization enclosure 1200 may include one or more light source 1206 that is designed to emit light having a frequency that injures pathogens. For example, the light emitted by the light source 1206 may have a germicidal ultraviolet short wavelength (i.e., between 230 and 310 nanometers (nm, 0.009056 thousandths of an inch (mils) and 0.0122 mils), between 240 and 300 nm (0.00945 mils and 0.0118 mils), between 255 and 280 nm (0.0100 mils and 0.0110 mils), or the like).

The main body 1202 may have a bottom surface 1207, two side surfaces 1209 (only one side surface is shown in FIG. 12 for illustration purposes), and a back surface 1211. The sterilization enclosure 1200 may include one or more front light source 1208 located towards a front 1213 of the main body 1202, may have a plurality of bottom light sources 1210 located along the bottom surface 1207, may include one or more side light source 1212 located on the side surfaces 1209, may include one or more back light source 1214 located on the back surface 1211, and so forth.

Referring to FIGS. 12 and 16A through 16C, the sterilization enclosure 1200 may include a movable component. For example, the movable component may be a retractable cover 1600. The retractable cover 1600 may have a top surface 1602 and a bottom surface 1604. The retractable cover 1600 may include a plurality of light sources 1606 on the bottom surface 1604.

The retractable cover 1600 may include multiple bendable grooves 1608 that provide flexibility of the retractable cover 1600. The retractable cover 1600 may be designed to slide along a track 1218 on each of the side surfaces 1209 of the main body 1202. The retractable cover 1600 may have an access position (i.e., a retracted position) in which the retractable cover 1600 is retracted to allow access to the cavity 1204. The retractable cover 1600 may further have a restricted position (i.e., an extended position) in which the retractable cover 1600 covers at least a portion of the cavity 1204 to restrict access to the cavity 1204.

When the retractable cover 1600 is in the extended position, the cavity 1204 is exposed to the light source 1606 on the bottom surface 1604 of the retractable cover 1600, thus allowing the light source 1606 (along with the light sources 1208, 1210, 1212, 1214) to sterilize any object in the cavity 1204.

The retractable cover 1600 may be coupled to a belt 1220 that is coupled to a motor 1222. The motor 1222 may drive operation of the belt 1220 which may in turn move the retractable cover 1600 between the retracted position and the extended position.

Returning reference to FIG. 12, the sterilization enclosure 1200 may include a controller 1224. The controller 1224 may control operation of the sterilization enclosure 1200. For example, the controller 1224 may control whether any or all of the light sources 1206 (including the light sources 1606 of the retractable cover 1600 of FIG. 16B) emit light. The controller 1224 may further control operation of the motor 1222.

The sterilization enclosure 1200 may further include a display 1250. The display 1250 may output the status of the sterilization enclosure 1200. For example, the display 1250 may include 3 LEDs, each of a different color. For example, the display 1250 may include a red LED, a yellow LED, and a green LED. Prior to sterilization of the cavity 1204, the red LED may be illuminated, indicating that the cavity 1204 is unsterilized. As the light source 1206 begins to emit light into the cavity 1204, the yellow LED may be illuminated to indicate that the cavity 1204 is being sterilized. After a sufficient amount of time has passed (corresponding to an amount of time sufficient for the light source 1206 to sterilize objects in the cavity 1204) the green LED may be illuminated to indicate that the cavity is fully sterilized. In some embodiments, other display types may be used, such as a CRT, LCD, ELD, or other display.

The sterilization device 1200 may further include a network access device 1226. The network access device 1226 may facilitate a wired or wireless connection to any remote device. For example, the network access device 1226 may communicate with a remote device via Bluetooth, Wi-Fi, Ethernet, or the like. The network access device 1226 may further be connected to the controller 1224. In that regard, the controller 1224 may control operation of the light source 1206 and the movable component (such as the retractable cover 1600 of FIG. 16A) based on signals received from the network access device 1226. Furthermore, the controller 1224 may identify faulty components of the sterilization enclosure 1200 and may transmit identification of the faulty components to a remote device to make a third party aware of the potentially faulty component such that it can be repaired.

Figure 13:
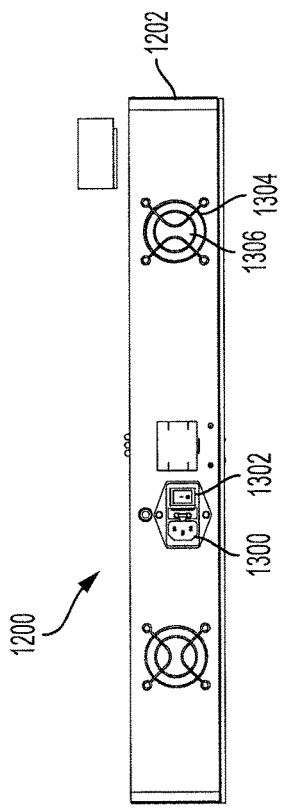
FIG. 13 is a drawing illustrating a rear view of the sterilization enclosure of FIG. 12 according to various embodiments of the present disclosure.

Referring now to FIGS. 12 and 13, the sterilization enclosure 1200 may include an electrical socket 1300 and a power switch 1302. The components of the sterilization enclosure 1200 may receive electrical power via the electrical socket 1300. Operation of the sterilization enclosure 1200 may be performed based on the status of the power switch 1302. For example, if the power switch 1302 is in an off position than the components of the sterilization enclosure 1200 may fail to receive electrical power.

The sterilization enclosure 1200 may further include one or more fan 1304 that at least one of draws air into the cavity 1204 or blows the air out of the cavity 1204. The sterilization enclosure 1200 may further include a filter 1306 that reduces the likelihood of particles being drawn into, or blown out of, the cavity 1204. The filter may capture particles and prevent them from being reintroduced into the air. In some embodiments, the filter 1306 may be replaceable. In that regard, an operator may periodically replace the filter 1306 with a new filter 1306.

Figure 14:
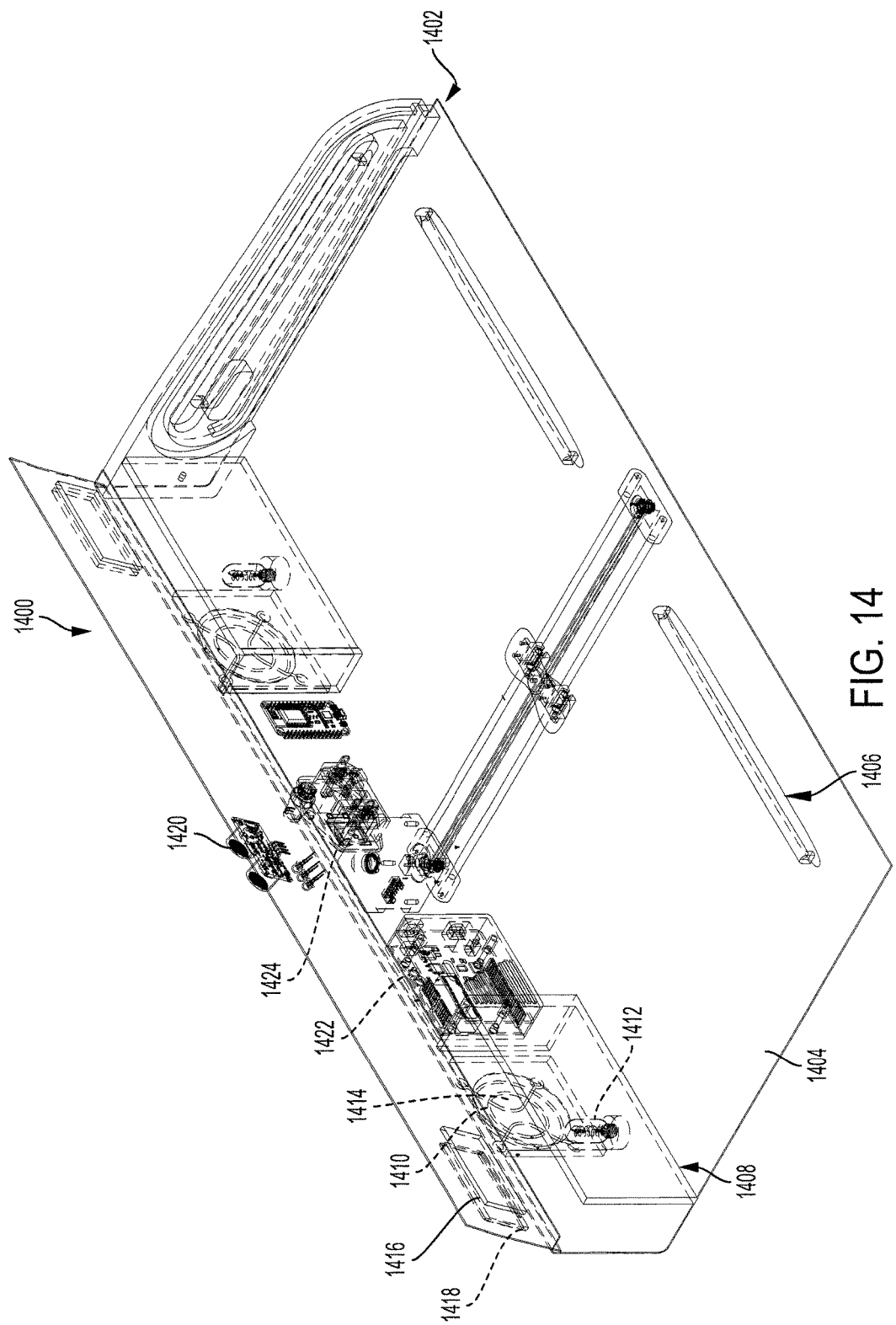
FIG. 14 is a drawing of another sterilization enclosure having additional features for sterilizing air in a surrounding environment according to various embodiments of the present disclosure.
Figure 15:
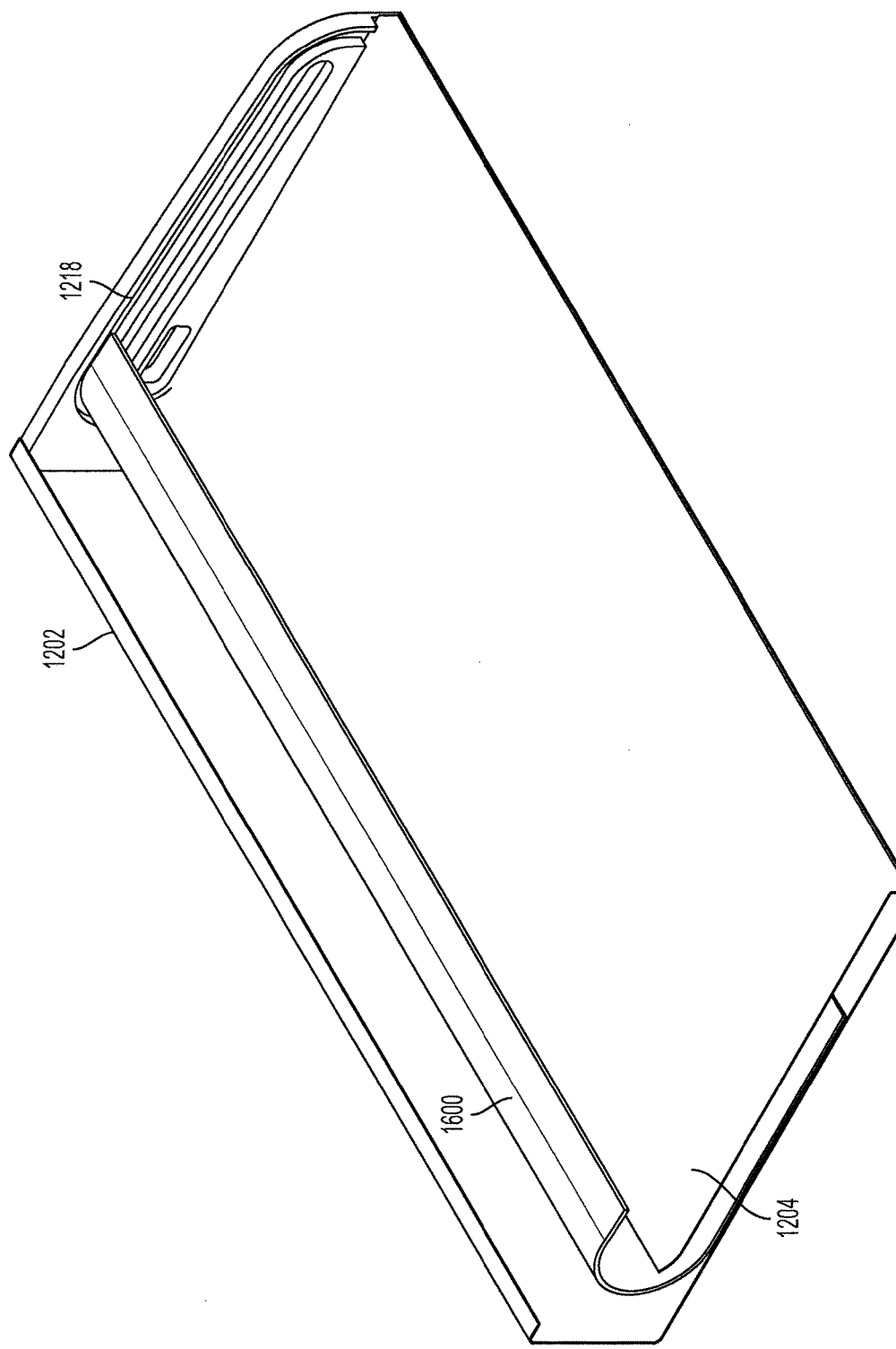
FIG. 15 is a drawing illustrating a retractable cover of a sterilization enclosure in an access (or retracted) position according to various embodiments of the present disclosure.

Turning now to FIG. 14, another sterilization enclosure 1400 is shown. The sterilization enclosure 1400 includes a main body 1402 that defines a cavity 1404. The sterilization enclosure 1400 may include one or more light source 1406 that emits light into the cavity 1404. The sterilization enclosure 1400 may further include features similar to the sterilization enclosure 1200 of FIG. 12 that allow the sterilization enclosure 1400 to operate with the retractable cover illustrated in FIGS. 16A through 16C such that additional light may be provided into the cavity 1404 by the light sources 1606 of the retractable cover 1600 of FIG. 16B.

The sterilization enclosure 1400 may further include one or more air sterilization cavity 1408. The air sterilization cavity 1408 may or may not be isolated from the main cavity 1404. The air sterilization cavity 1408 may include a fan 1410 that draws air into (or forces air out of) the air sterilization cavity 1408. The air sterilization cavity 1408 may further include an additional light source 1412 designed to sterilize air within the air sterilization cavity 1408. The additional light source 1412 may have a relatively large surface area to facilitate sterilization of a relatively large volume of air at once.

The air sterilization cavity 1408 may include an inlet 1414 and an outlet 1416. Air may be drawn into the air sterilization cavity 1408 via the inlet 1414 and may exit via the outlet 1416. A filter 1418 may be included at the outlet 1416 (or in some embodiments at the inlet 1414) and may filter the air leaving the air sterilization cavity 1408. The fan 1410 may draw air into the air sterilization cavity 1408, the additional light source 1412 may sterilize the air, and the air may be blown back into the environment via the outlet 1416 as sterilized air. In that regard, the sterilization enclosure 1400 may operate both to sterilize (i.e., injure pathogens) present on components within the main cavity 1404 as well as sterilize air in an environment in which the sterilization enclosure 1400 is located.

The sterilization enclosure 1400 may include a sensor 1420. The sensor 1420 may detect an open event corresponding to a desire for access to the cavity 1404, and may detect a close event corresponding to a desire for the light source to emit the light to sterilize the cavity 1404. For example, the sensor 1420 may include a motion sensor or other sensor capable of detecting a presence of a person or a gesture by the person. The open event may include a detected presence of a person or a specific gesture. The close event may include a lack of presence of a person or another specific gesture.

The sterilization enclosure 1400 may include a controller 1422 that controls operation of a motor 1424 (to open and close a retractable cover) and the light source 1406. For example, when the sensor detects the open event, the controller 1422 may control the light source 1406 to cease emitting light and may control the retractable cover to open to allow access to the cavity 1404. When the sensor detects the close event, the controller 1422 may control the retractable cover to close to restrict access to the cavity 1404 and may control the light source 1406 to emit the light to sterilize the cavity 1404.

Referring now to FIGS. 12, 15, and 16A-16C, the main body 1202 may define the track 1218 within which the retractable cover 1600 is located. The retractable cover 1600 may travel along the track 1218 until the retractable cover 1600 entirely covers or encloses the cavity 1204 defined by the main body 1202.

Figure 17B:
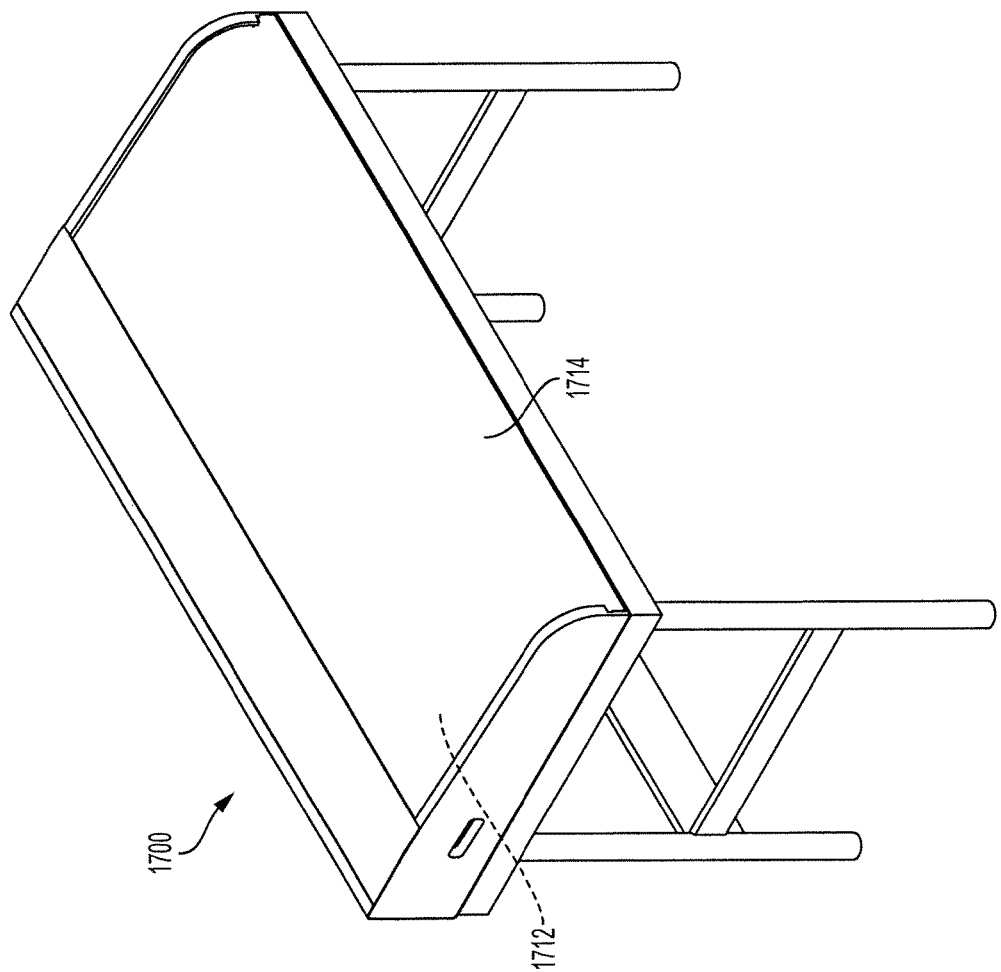

Referring now to FIGS. 17A and 17B, another sterilization enclosure 1700 is shown. The sterilization enclosure 1700 has a main body 1702 that resembles a desk and includes four legs 1704 and a surface 1706. The main body 1702 further includes at least three sides 1708 positioned about the surface 1706, defining a cavity 1712. At least one of the sides 1708 includes a track 1710.

The sterilization enclosure 1700 further includes a retractable cover 1714. For example, the retractable cover 1714 may have similar features as the retractable cover 1600 of FIGS. 16A-16C, such as one or more light source that outputs light having a frequency that injures pathogens. As shown in FIG. 17B, the retractable cover 1714 may completely enclose the cavity 1712 such that light emitted by the retractable cover 1714 sterilizes any items left in the cavity 1712.

The sterilization enclosure 1700 may be used by multiple individuals each day. For example, the sterilization enclosure 1700 may be located in a school and used by multiple schoolchildren each day. Between each class, a controller of the sterilization enclosure 1700 may cause the retractable cover 1714 to move to the restricted position and cause the light source of the retractable cover 1714 to sterilize the cavity 1712. Prior to beginning of the following class, the controller may cause the retractable cover 1714 to move to the access (retracted) position, providing a sterilized surface 1706 for the next student to use.

Figure 18:
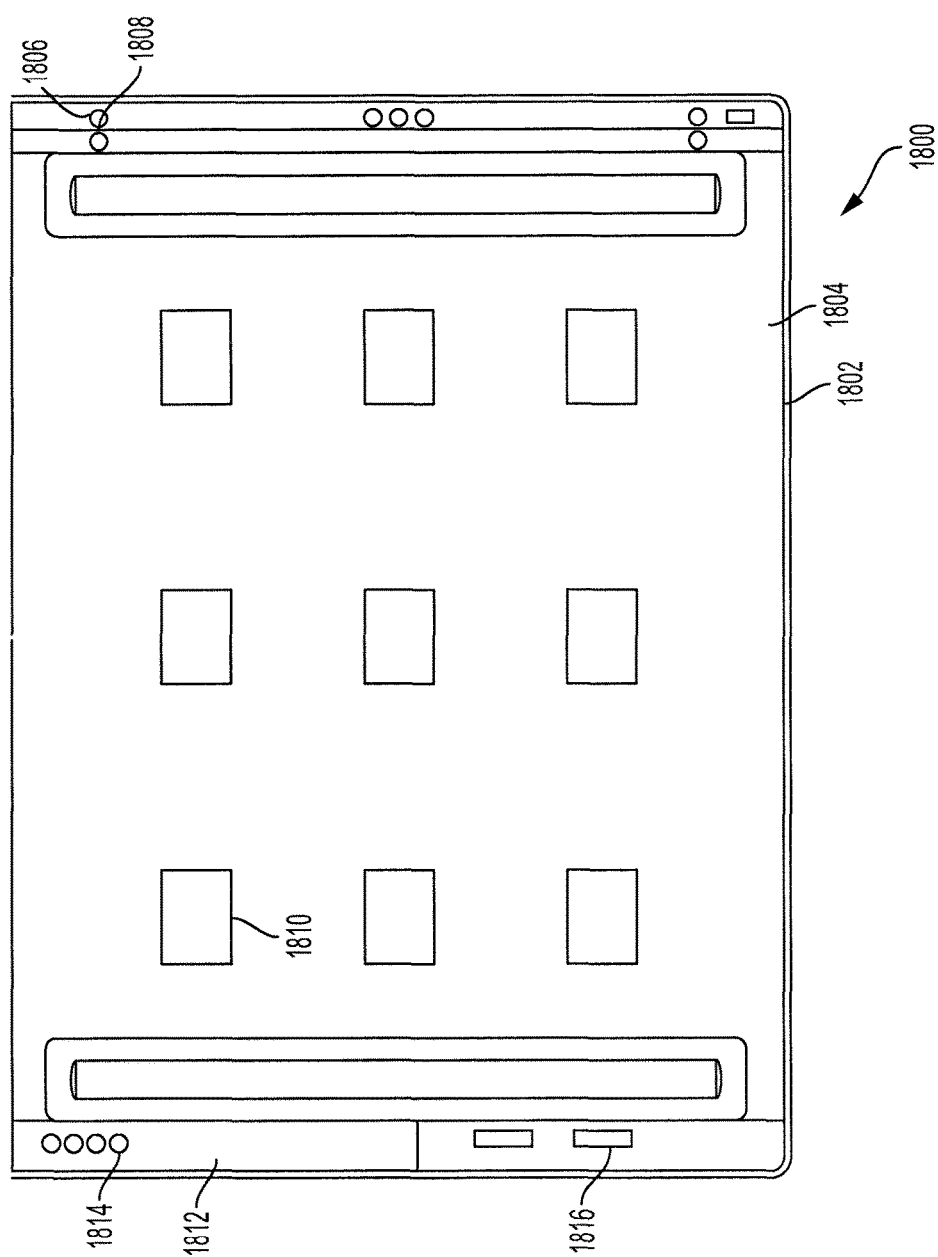
FIG. 18 is a drawing illustrating a sterilization enclosure capable of being used as a purse, briefcase, or other tote according to various embodiments of the present disclosure.

Turning now to FIG. 18, another sterilization enclosure 1800 is shown. The sterilization enclosure 1800 may function as a bag, suitcase, pocketbook, or other tote such as a suitcase. In that regard, the sterilization enclosure 1800 may include a main body 1802 that defines a cavity 1804. The sterilization enclosure 1800 may further include a fastener 1806. The fastener 1806 may include, for example, a clip, a pair of magnets, or the like.

The sterilization enclosure 1800 may further include a switch 1808. The switch 1808 may be designed to switch between an open state when the fastener 1806 is unfastened and a closed state when the fastener 1806 is fastened.

An inner surface of the main body 1802 may include a plurality of light sources 1810. The light sources 1810 may emit light having a frequency that injures pathogens.

The sterilization enclosure 1800 may further include a power source 1812, such as one or more battery. The sterilization enclosure 1800 may also include a battery indicator 1814 that indicates a current status of the power source 1812. The sterilization enclosure 1800 may further include one or more port 1816 that facilitates charging of the power source 1812. For example, the port 1816 may include a USB port that receives power for charging the power source 1812, such as a battery.

The switch 1808 may be coupled between the power source 1812 and the light source 1810. When the sterilization enclosure 1800 is fastened using the fastener 1806, the switch 1808 may switch to a closed state to allow power to flow from the power source 1812 to the light source 1810 to cause the light source 1810 to emit the light. When the fastener 1806 is unfastened, the switch 1808 may switch to an open state to reduce the likelihood of power flowing from the power source 1812 to the light source 1810. This reduces the likelihood of a human being exposed to the light, which may be hazardous to a human. In some embodiments, a controller may cause the light source 1810 to emit the light for a predetermined period of time only after the sterilization enclosure 1800 is fastened in order to save power.

Figure 19:
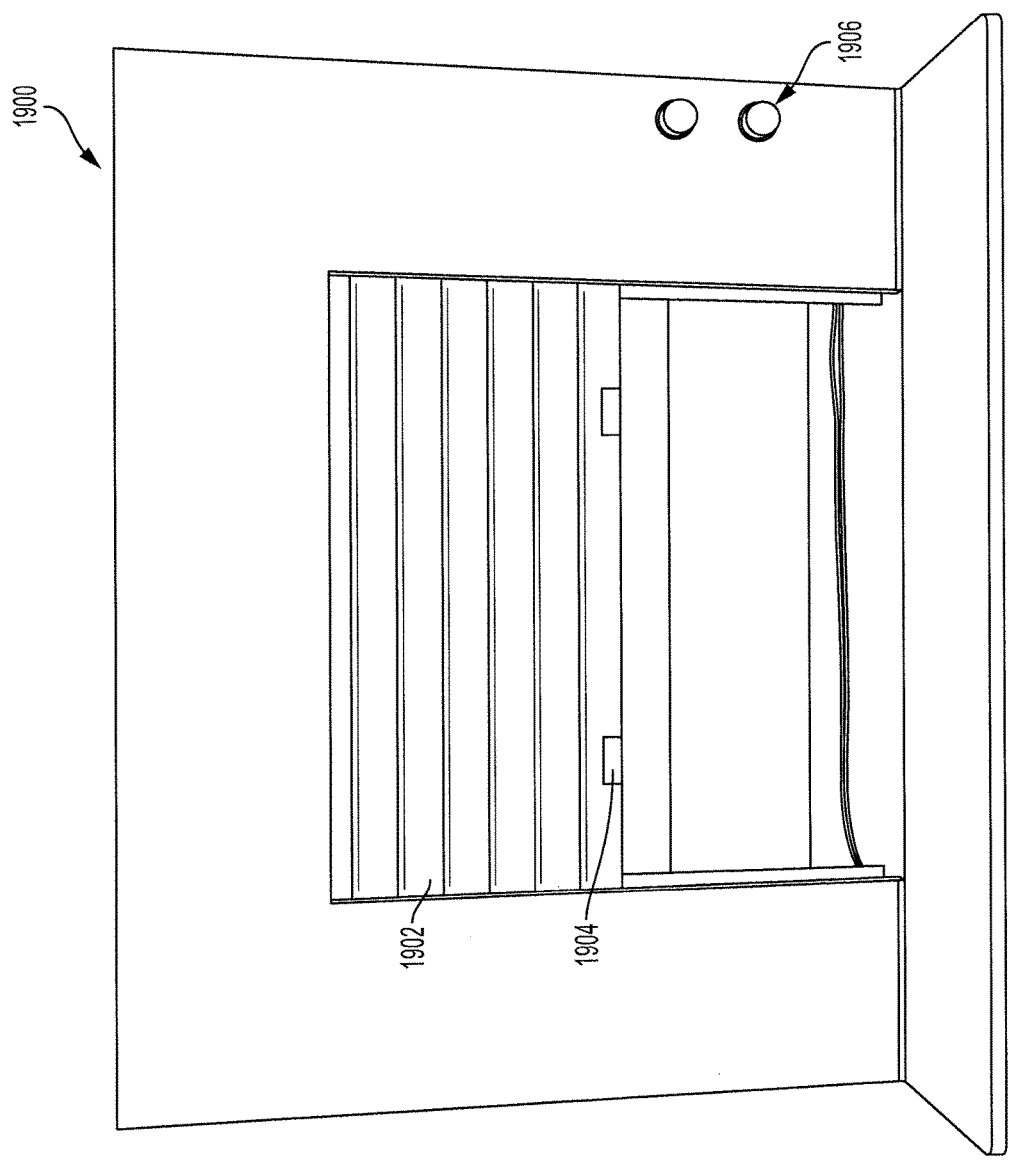
FIG. 19 is a drawing illustrating a vertical sterilization enclosure according to various embodiments of the present disclosure.

Referring to FIG. 19, another sterilization enclosure 1900 is shown. The sterilization enclosure 1900 may be oriented vertically. For example, the sterilization enclosure 1900 may be located in front of a door handle, an elevator button, or the like. The sterilization enclosure 1900 may include a vertically-movable component 1902, which may be a retractable cover 1904. One or more light source that emits sterilizing light may be located on an opposing side of the retractable cover 1904.

The sterilization enclosure 1900 may include a sensor 1906. The sensor 1906 may include a button, a motion detector, or the like and may be used to control operation of the sterilization enclosure 1900. For example, the sterilization enclosure 1900 may be located in front of an elevator button. If a user wishes to the press the elevator button, the user may waive his or her hand in front of the sensor 1906, thus causing the retractable cover 1904 to retract to allow access to the elevator button. After remaining in the retracted position for a predetermined period of time (such as 10 seconds, 20 seconds, 30 seconds, or the like), the retractable cover 1904 may return to the restricted position to at least partially enclose the elevator button and the light source may illuminate in order to sterilize any pathogens that may have been transmitted to the elevator button by the user.

Figure 20:
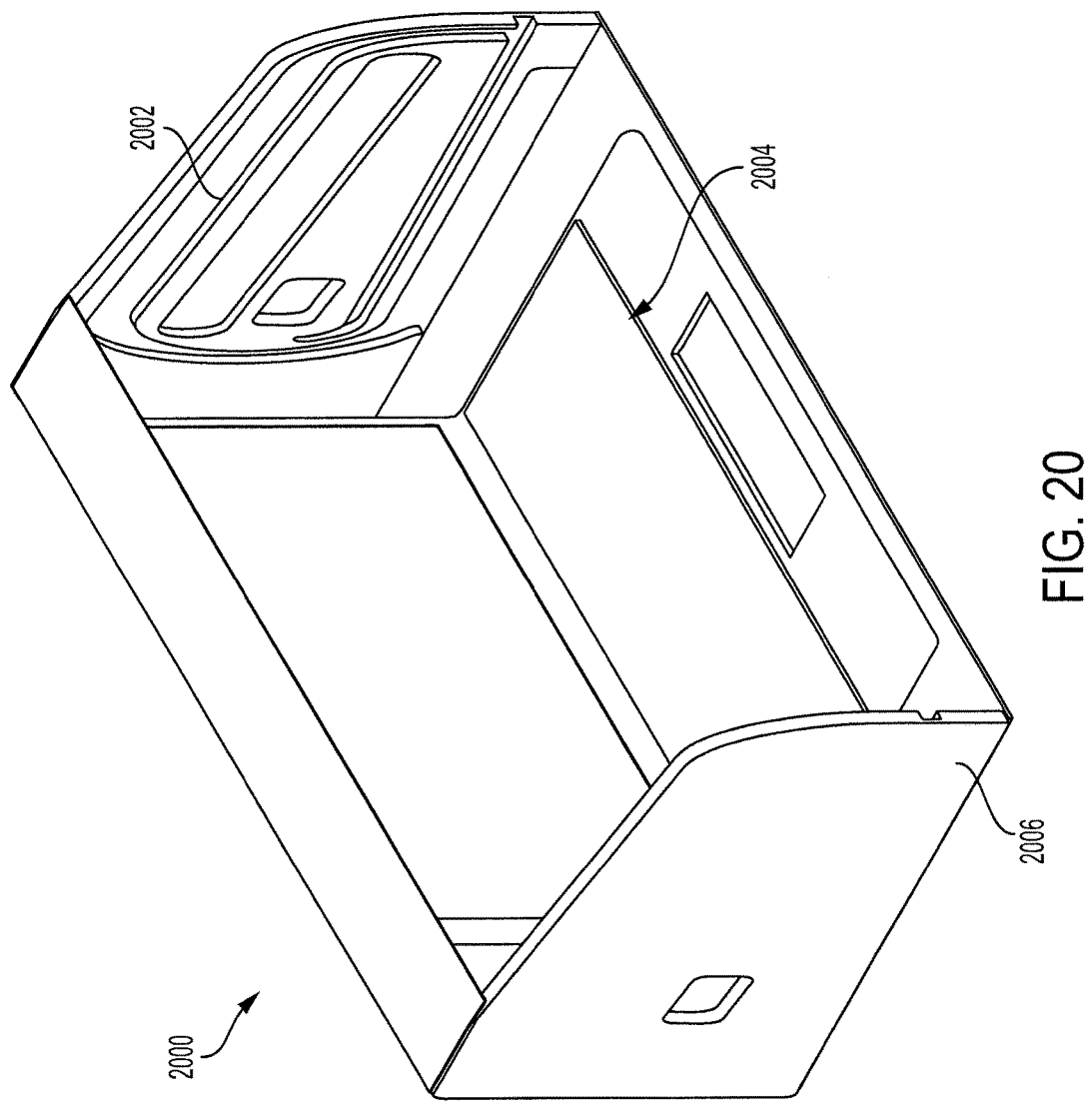
FIG. 20 is a drawing illustrating a sterilization enclosure for use with a laptop or other computing device according to various embodiments of the present disclosure.

Turning to FIG. 20, another sterilization enclosure 2000 is shown. The sterilization enclosure 2000 may be designed specifically for use with a laptop or other computing device. In particular, the sterilization enclosure 2000 may have a main body 2006 that is designed to have slightly larger dimensions than a laptop or other computing device 2004. In that regard, the laptop or other computing device 2004 may fit entirely within the main body 2006. The main body 2006 may include a tract 2002 that is designed for use with a retractable cover, such as the retractable cover 1600 of FIG. 16.

When the retractable cover is in the restricted position, the laptop 2004 may be entirely enclosed within the main body 2006 and the retractable cover. The sterilization enclosure 2000 may include a sensor that detects presence of a person in front of the laptop or other computing device 2004. In that regard, the retractable cover of the sterilization enclosure 2000 may remain closed (in the restricted position) until a user is detected in front of the sterilization enclosure 2000. In response to detection of the user, the retractable cover may retract to the access position, thus allowing the user to use the laptop or other computing device 2004. When the sensor detects that the user is no longer in front of the sterilization enclosure 2000, a controller may control the retractable cover to close to the restricted position and may cause one or more light source to emit light having a frequency to injure or otherwise sanitize pathogens that may be left behind on the laptop or other computing device 2004.

Figure 21B:
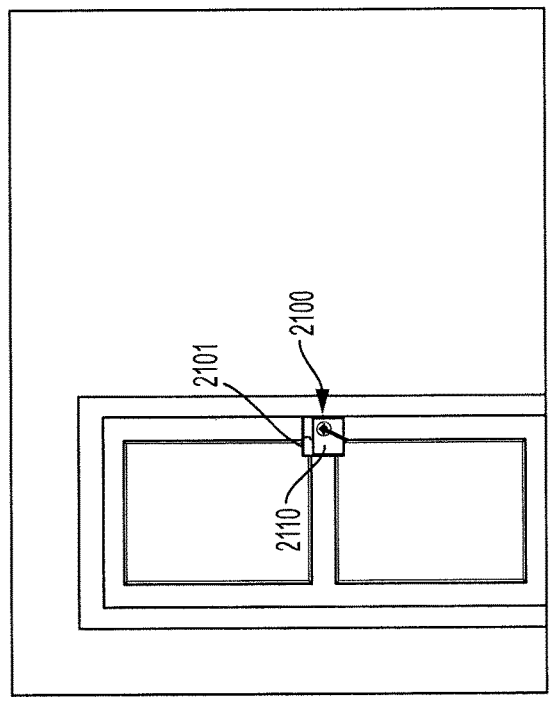
FIGS. 21A and 21B are drawings illustrating a sterilization enclosure for use with a door handle to sterilize the door handle according to various embodiments of the present disclosure.
Figure 21A:
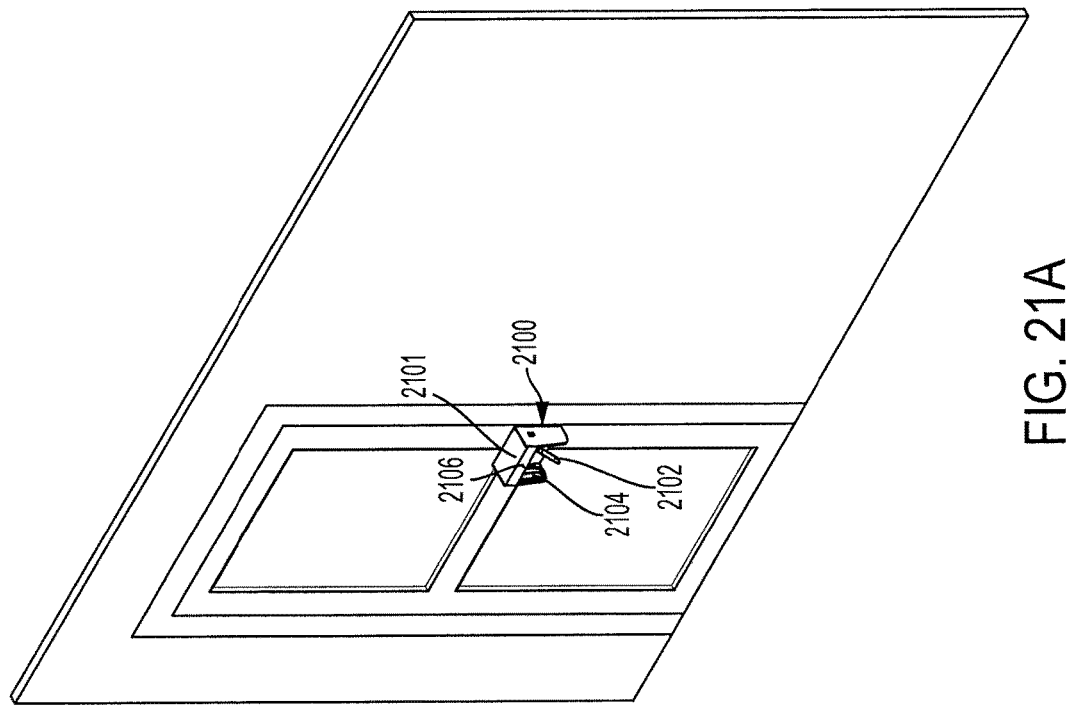
Figure 22A:
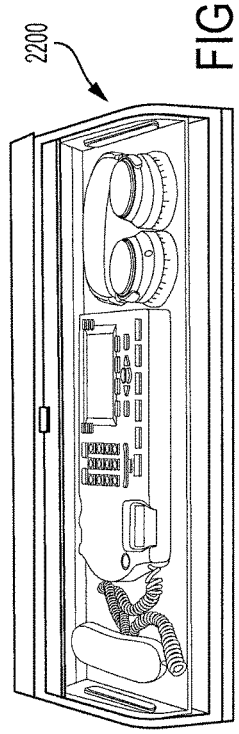
FIGS. 22A-22E are drawings illustrating sterilization enclosures of various sizes according to various embodiments of the present disclosure.
Figure 22C:
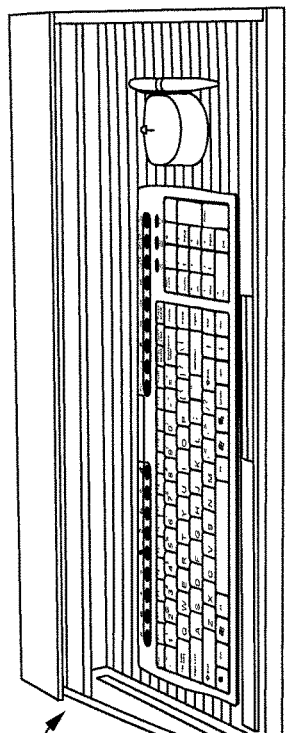
Figure 22B:
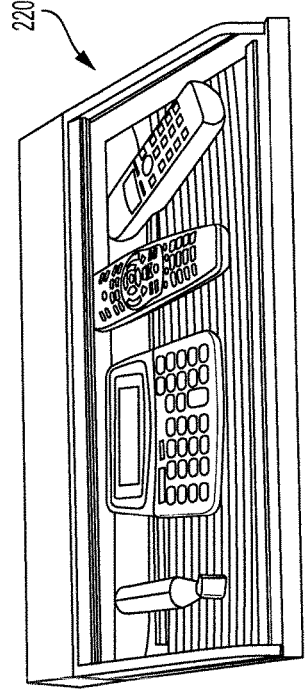
Figure 22E:
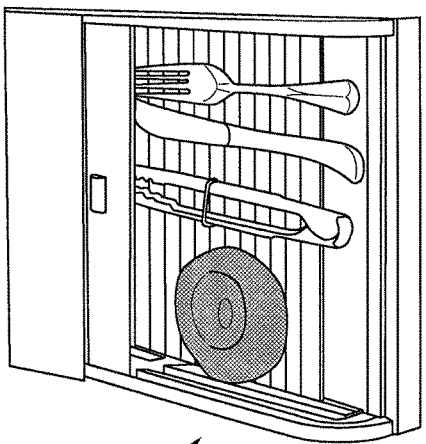
Figure 22D:
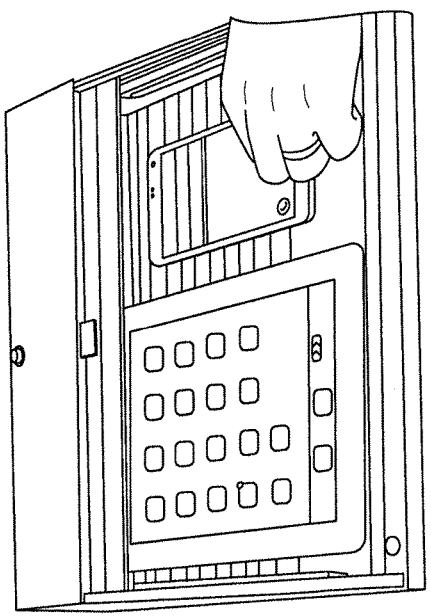

Turning now to FIGS. 21A and 21B, a sterilization enclosure 2100 may be designed for use with a door handle. In that regard, a main body 2101 may be mounted to a door such that a retractable cover 2110 covers a door handle 2102 when in the restricted position.

The sterilization enclosure 2100 may include a sensor 2106. The sensor 2106 may detect the presence of a user. For example, the sensor 2106 may detect when a user is approaching the sterilization enclosure 2100. As the user approaches the sterilization enclosure 2100, the retractable cover 2110 of the sterilization enclosure 2100 may retract, thus allowing access to the door handle 2102.

The sterilization enclosure 2100 may further include a light source 2104 that emits light having a frequency that injures pathogens. After the user uses the door handle 2102 to enter or leave a room, the sensor 2106 may detect a lack of presence of a person. In response to the detected lack of presence, a controller may control the retractable cover 2110 to move to the restricted position to cover the door handle 2102 and may simultaneously control the light source 2104 to emit the light. In some embodiments, the controller may control the light source 2104 to emit the light for a predetermined period of time and may control the retractable cover 2110 to remain in the restricted position (i.e., covering the door handle 2102) until another user approaches the sterilization enclosure 2100. In some embodiments, the controller may control the light source 2104 to emit the light for a predetermined period of time and may control the retractable cover 2110 to retract to the access position after expiration of the predetermined period of time.

Referring now to FIGS. 22A-22D, sterilization enclosures may be provided having various sizes. For example, a first sterilization enclosure 2200 may be referred to as an extra-large sterilization enclosure and may have dimensions of about 24 inches (61 cm) in length, about 12.5 inches (32 cm)

in width, and about 4.5 inches (11 cm) in height. Where used in this context, about refers to the stated value plus or minus 10% of the stated value.

Another sterilization enclosure 2202 may be referred to as a large sterilization enclosure and may have dimensions of about 24 inches (61 cm) in length, about 12 inches (30 cm) in width, and about 3 inches (7.6 cm) in height.

Another sterilization enclosure 2204 may be referred to as a medium sterilization enclosure and may have dimensions of about 19 inches (48 cm) in length, about 12 inches (30 cm) in width, and about 3 inches (7.6 cm) in height.

Another sterilization enclosure 2206 may be referred to as a small sterilization enclosure and may have dimensions of about 14 inches (36 cm) in length, about 12 inches (30 cm) in width, and about 3 inches (7.6 cm) in height.

Another sterilization enclosure 2208 may be referred to as an extra small sterilization enclosure and may have dimensions of about 10 inches (25 cm) in length, about 12 inches (30 cm) in width, and about 3 inches (7.6 cm) in height.

In some embodiments, a single sterilization enclosure may be provided that is adjustable in size. In that regard, the single sterilization enclosure may be adjustable to have the dimensions of any of the sterilization enclosures 2200, 2202, 2204, 2206, 2208.

Figure 23:
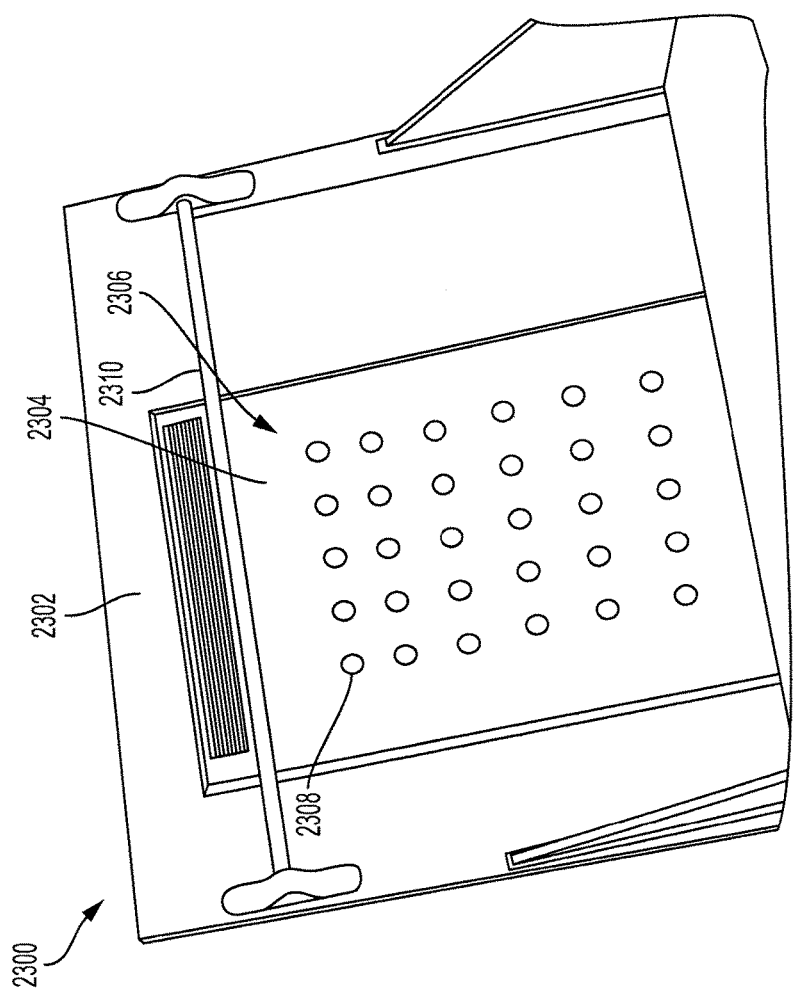
FIG. 23 is a drawing illustrating a sterilization enclosure having a sliding door as a movable component according to various embodiments of the present disclosure.

Referring now to FIG. 23, another sterilization enclosure 2300 is shown. The sterilization enclosure 2300 may have a sliding door 2304 as the movable component 2306. In particular, the sliding door 2304 may slide along one or more track 2310.

The sterilization enclosure 2300 may include one or more light source 2308 that emits light having a frequency capable of injuring pathogens. In that regard, the sterilization enclosure 2300 may be mounted to cover an item in which pathogens may transfer from person to person. For example, the sterilization enclosure 2300 may be mounted to cover a light switch. A sensor may detect a person approaching the light switch and may cause the sliding door 2304 to slide to an access position to allow access to the light switch. When the sensor no longer detects the person (or after a predetermined amount of time has expired since the lack of detection of the person) a controller may cause the sliding door 2304 to slide back to the restricted position and may cause the light source 2308 to emit the light to injure any pathogens left behind on the light switch.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A sterilization enclosure comprising:
   a main body defining a volume and an air sterilization cavity that is isolated from the volume;
   a retractable cover configured to move between an access position in which the retractable cover is retracted to allow access to the volume and a restricted position in which the retractable cover at least partially encloses the volume;
   a motor coupled to the retractable cover and configured to move the retractable cover between the access position and the restricted position;
   a cavity light source located in the volume and configured to emit light having a frequency that injures pathogens;
   a sensor configured to detect motion;
   a secondary light source positioned in the air sterilization cavity and configured to emit light having the frequency or another frequency that injures pathogens to sterilize air in the air sterilization cavity;
   a fan coupled to the main body and configured to at least one of draw the air into or blow the air out of the air sterilization cavity while the cavity light source is emitting the light, the cover is in the restricted position, and the secondary light source is emitting the light such that the cavity light source can sterilize an object in the cavity as the fan simultaneously at least one of draws the air into or blows the air out of the air sterilization cavity in order to direct sterilized air into an environment surrounding the main body;
   a wireless network access device coupled to the controller and configured to receive a signal indicating at least one of an open request corresponding to a first request for access to the volume or a close request corresponding to a second request for sterilization of the volume; and
   a controller coupled to the motor, the cavity light source, the sensor, and the wireless network access device, and configured to control the motor to move the retractable cover between the restricted position and the access position and to control the cavity light source to emit the light based on the detected motion, to move the retractable cover to the restricted position and to control the cavity light source to emit the light in response to the received signal including the close request, and to control the motor to move the retractable cover to the access position in response to the received signal including the open request.

2. The sterilization enclosure of claim 1 wherein the sensor is further configured to detect an open event corresponding to a desire for access to the volume, and the controller is further configured to control the motor to move the retractable cover to the access position in response to the sensor detecting the open event.

3. The sterilization enclosure of claim 1 wherein the sensor is further configured to detect a close event corresponding to a desire for the cavity light source to emit the light, and the controller is further configured to control the retractable cover to be in the restricted position and to control the cavity light source to emit the light in response to the sensor detecting the close event.

4. The sterilization enclosure of claim 3 wherein the close event includes at least one of a lack of presence of a person or a gesture.

5. The sterilization enclosure of claim 3 wherein the controller is further configured to control the retractable cover to be in the restricted position and to control the cavity light source to emit the light for a predetermined amount of time after the sensor detects the close event, and then to control the cavity light source to cease emitting the light and the retractable cover to be in the access position after expiration of the predetermined amount of time.

6. The sterilization enclosure of claim 1 wherein the main body includes at least two sides that each define a curved track within which the retractable cover is positioned such that the retractable cover can move along the curved track between the access position and the restricted position.

7. The sterilization enclosure of claim 1 wherein the main body has an adjustable size having at least a first size that causes the volume to have a first area and a second size that causes the volume to have a second area that is less than the first area.

8. The sterilization enclosure of claim 1 wherein the cavity is defined by an inner surface that faces the volume and includes a material that is at least partially reflective in order to cause the light to reach all surfaces of the object within the volume when the cavity light source emits the light.

9. The sterilization enclosure of claim 1 wherein the main body includes a bottom, two sides, and a back, and the retractable cover is configured to move along a track that is curved towards a front of the main body in order to fully enclose the volume when in the restricted position to reduce a likelihood of the light escaping the volume.

10. The sterilization enclosure of claim 1 further comprising a filter coupled to the main body and configured to remove particles from the air as at least one of the air is being drawn into the air sterilization cavity or the air is being blown out of the air sterilization cavity.

11. The sterilization enclosure of claim 1 wherein the main body is configured to be mounted to a surface such that an object in public is enclosed within the volume when the retractable cover is in the restricted position.

12. The sterilization enclosure of claim 11 wherein the object includes at least one of a button or a door handle, and the retractable cover includes a sliding door.

13. A sterilization enclosure comprising:
a main body defining a volume;
a retractable cover configured to move between an access position in which the retractable cover is retracted to allow access to the volume and a restricted position in which the retractable cover at least partially encloses the volume;
a motor coupled to the retractable cover and configured to move the retractable cover between the access position and the restricted position;
a light source located in the volume and configured to emit light having a frequency that injures pathogens;
a sensor configured to detect motion;
a fan coupled to the main body and configured to at least one of draw air into or blow air out of the cavity while the light source is emitting the light and the retractable cover is in the restricted position in order to direct sterilized air from the cavity into an environment surrounding the main body;
a wireless network access device coupled to the controller and configured to receive a signal indicating at least one of an open request corresponding to a first request for access to the volume or a close request corresponding to a second request for sterilization of the volume; and
a controller coupled to the motor, the light source, the sensor, and the wireless network access device and configured to control the motor to move the retractable cover between the restricted position and the access position and to control the light source to emit the light based on the detected motion and to at least one of:
control the motor to move the retractable cover to the restricted position and control the light source to emit the light in response to the received signal including the close request, or
control the motor to move the retractable cover to the access position and control the light source to cease emitting the light in response to the received signal including the open request.

14. The sterilization enclosure of claim 13 wherein the sensor is further configured to detect an open event corresponding to a desire for access to the volume, and the controller is further configured to control the motor to move the retractable cover to the access position in response to the sensor detecting the open event.

15. The sterilization enclosure of claim 13 wherein the sensor is further configured to detect a close event corresponding to a desire for the light source to emit the light, and the controller is further configured to control the retractable cover to be in the restricted position and to control the light source to emit the light in response to the sensor detecting the close event.

16. The sterilization enclosure of claim 15 wherein the controller is further configured to control the retractable cover to be in the restricted position and to control the light source to emit the light for a predetermined amount of time after the sensor detects the close event, and then to control the light source to cease emitting the light and the retractable cover to be in the access position after expiration of the predetermined amount of time.

17. A sterilization enclosure comprising:
a main body defining a volume and including at least two sides that each define a track;
a retractable cover configured to move along the track of the at least two sides between an access position in which the retractable cover is retracted to allow access to the volume and a restricted position in which the retractable cover at least partially encloses the volume;
a motor coupled to the retractable cover and configured to move the retractable cover between the access position and the restricted position;
a light source located in the volume and configured to emit light having a frequency that injures pathogens;
a wireless network access device configured to receive a signal indicating at least one of an open request corresponding to a first request for access to the volume or a close request corresponding to a second request for sterilization of the volume; and
a controller coupled to the motor, the light source, and the wireless network access device and configured to at least one of:
control the motor to move the retractable cover to the restricted position and control the light source to emit the light in response to the received signal including the close request, or
control the motor to move the retractable cover to the access position and control the light source to cease emitting the light in response to the received signal including the open request.

18. The sterilization enclosure of claim 17 further comprising a sensor configured to detect a close event corresponding to a desire for the light source to emit the light, and the controller is further configured to:
control the retractable cover to be in the restricted position and control the light source to emit the light in response to the sensor detecting the close event;
control the retractable cover to be in the restricted position and control the light source to emit the light for a predetermined amount of time after the sensor detects the close event; and
control the light source to cease emitting the light and the retractable cover to be in the access position after expiration of the predetermined amount of time.

* * * * *